United States Patent
Osaka et al.

(10) Patent No.: US 8,708,912 B2
(45) Date of Patent: Apr. 29, 2014

(54) ULTRASOUND DIAGNOSTIC APPARATUS AND METHOD OF DISPLAYING ULTRASOUND IMAGE

(75) Inventors: Takashi Osaka, Chiba (JP); Takeshi Matsumura, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1464 days.

(21) Appl. No.: 11/719,414

(22) PCT Filed: Nov. 17, 2005

(86) PCT No.: PCT/JP2005/021112
§ 371 (c)(1),
(2), (4) Date: May 16, 2007

(87) PCT Pub. No.: WO2006/054635
PCT Pub. Date: May 26, 2006

(65) Prior Publication Data
US 2009/0124903 A1    May 14, 2009

(30) Foreign Application Priority Data
Nov. 17, 2004    (JP) .................................. 2004-333152

(51) Int. Cl.
*A61B 8/00*    (2006.01)

(52) U.S. Cl.
USPC ........... 600/443; 600/407; 600/437; 600/438; 600/439; 600/440; 600/442; 600/444; 600/445; 600/446; 600/447; 600/448; 600/458; 600/459

(58) Field of Classification Search
USPC ......... 600/437, 438, 439, 440, 443, 444, 445, 600/446, 447, 462, 463, 464; 128/915, 916; 604/19
See application file for complete search history.

(56) References Cited

U.S. PATENT DOCUMENTS 5,833,634 A * 11/1998 Laird et al. .................... 600/587
5,911,694 A * 6/1999 Ikeda et al. .................... 600/587

(Continued)

FOREIGN PATENT DOCUMENTS

| CN | 1498598 | 5/2004 |
|---|---|---|
| JP | 63-230155 | 9/1988 |

(Continued)

OTHER PUBLICATIONS

"Diagnosis of prostate carcinoma using multicompression strain imaging: data acquisition and first in vivo results" by A. Lorenz, H.J. Sommerfeld, M.G. Schurmann, S. Philippou, Th. Senge, and H. Ermert. IEEE Ultrasonics Symp. 98. pp. 1761-1764 (1998).*

(Continued)

*Primary Examiner* — Tse Chen
*Assistant Examiner* — Jason Ip
(74) *Attorney, Agent, or Firm* — Antonelli, Terry, Stout & Kraus, LLP.

(57) ABSTRACT

Ultrasound diagnostic apparatus includes an unit 7 for forming time series tomographic images on the basis of a reflection echo signals received by ultrasound probe 2, an unit 8 for obtaining the elasticities of body tissue on the basis of the reflection echo signals and forming elasticity images on times series, an unit 9 for forming a superimposition image on time series by superposing the tomographic image on the elasticity image, an unit 43 for inputting an instruction for controlling superimposition image formation, and an unit 10 for displaying the superimposition image. The ultrasound diagnostic apparatus further includes a freezing control portion (7, 8) for outputting an image, as a frozen image, selected in response to a freezing instruction for freezing the display operation on time series of any of the tomographic image or the elasticity image input into the input unit to the superimposition image forming unit.

16 Claims, 17 Drawing Sheets

(56) References Cited

U.S. PATENT DOCUMENTS

| | | | |
|---|---|---|---|
| 6,004,270 A * | 12/1999 | Urbano et al. | 600/443 |
| 6,171,248 B1 * | 1/2001 | Hossack et al. | 600/459 |
| 6,175,756 B1 * | 1/2001 | Ferre et al. | 600/424 |
| 6,450,961 B1 | 9/2002 | Shiki et al. | |
| 6,638,221 B2 * | 10/2003 | Abe et al. | 600/437 |
| 2002/0133075 A1 * | 9/2002 | Abdelhak | 600/443 |
| 2003/0135116 A1 | 7/2003 | Ogasawara et al. | |
| 2004/0015079 A1 | 1/2004 | Berger | |
| 2004/0034304 A1 | 2/2004 | Sumi | |

FOREIGN PATENT DOCUMENTS

| | | |
|---|---|---|
| JP | 01-139044 | 5/1989 |
| JP | 2000-060853 | 2/2000 |
| JP | 2000-060857 | 2/2000 |
| JP | 2004-135934 | 5/2004 |
| WO | WO 2004/041092 | 5/2004 |

OTHER PUBLICATIONS

"An algorithm for automatic needle localization in ultrasound-guided breast biopsies" by K.J. Draper, C.C. Blake, L. Gowman, D.B. Downey, and A. Fenster. Am. Assoc. Phys. Med. 8. pp. 1971-1979 (2000).*

Japanese Office Action, dated Apr. 12, 2011, issued in corresponding Japanese Patent Application No. 2006-545124.

* cited by examiner

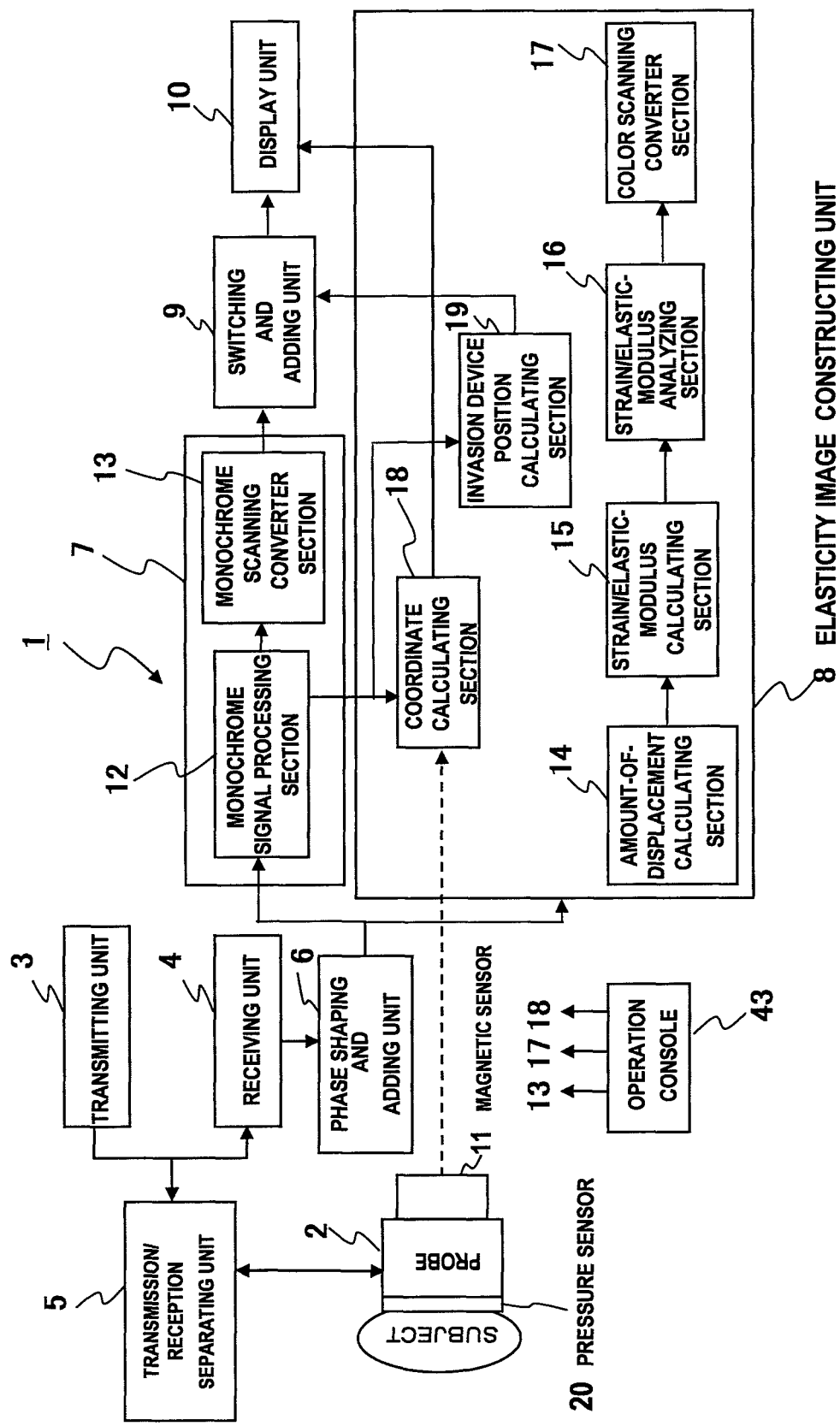

ULTRASOUND DIAGNOSTIC APPARATUS AND METHOD OF DISPLAYING ULTRASOUND IMAGE

TECHNICAL FIELD

The present invention relates to an ultrasound diagnostic apparatus and a method of displaying ultrasound image, and more particularly, to an ultrasound diagnostic apparatus and a method of displaying ultrasound image that can display an elasticity image and a tomographic image of the living body in a display format suitable to diagnostic operation.

BACKGROUND ART

An ultrasound diagnostic apparatus iteratively transmits ultrasonic waves from an ultrasound probe to a subject at the time interval, the ultrasound probe receives reflection echo signals on time series corresponding to the iterative transmission of the ultrasonic waves, a receiving-signal processing unit generates high-frequency (RF) frame data corresponding to arbitrary tomographic planes of the subject on time series on the basis of the received reflection echo signal, and tomographic images (e.g., B-mode images) on time series are restructured and displayed on the basis of the RF frame data, thereby using the ultrasound diagnostic apparatus for medical diagnosis.

For the above-mentioned ultrasound diagnostic apparatus, in recent years, such a technology is proposed that the elastic modulus and strain of the body tissue in the diagnostic part are measured and are displayed as an elasticity image (refer to e.g., Patent Document 1). As mentioned above, the subject is iteratively pressurized (compressed and decompressed), the elasticity image is obtained with the strain of the body tissue of the subject due to the pressure on the basis of two pieces of the FR frame data on time series, the elasticity (strain or elastic modulus) of each part of the body tissue is obtained, and the elasticity image is displayed in a display format (color image or binary image) corresponding to the level of elasticity.

In the medical diagnosis, in the case of diagnosing the diseased tissue such as cancer, a specific substance in the blood having a relationship with the diseased tissue is generally examined with blood drawing. For example, as diagnosis of the prostate cancer, PSA (Prostate Specific Antigen) examination is well-known. The PSA is a substance generated in the prostate, so-called prostate-specific antigen. In the case of the prostate cancer, the blood level increases and the blood of a patient is therefore sampled and the blood level in the PSA is examined, thereby diagnosing the prostate cancer. The PSA examination can be performed only with the blood sampling. Thus, in the case of suspecting the prostate cancer, the PSA examination is first performed and a patient having a high PSA value undergoes the ultrasonography or MRI examination.

However, even if the PSA value is high, a cancer cannot determined by the examination using the ultrasound image or MR image. Therefore, the organ of prostate is directly sampled with an invasion device such as a paracentesis needle, thereby performing the diagnosis (cytology). However, upon sampling the organ of the lesion, the lesion which is suspected to have a cancer cannot be specified out of the body. As a consequence, the paracentesis is actually executed to the lesion at random plural times. The number of paracentesis times is varied depending on the medical facility. Further, even with the paracentesis, a cancer cell cannot be found. Therefore, there is a problem that the examination takes a long time and the operation strains the patient.

Herein, the lesion of the cancer, etc. has the elasticity of organ higher than that of the normal organ around the lesion. Therefore, an elasticity image indicating the hardness of organ with an ultrasound diagnostic apparatus is formed, thereby enabling the position of the lesion to be specified. Then, upon invading a paracentesis needle in the living body, a color elasticity image of the lesion is superposed to a B-mode tomographic image and the resultant image is displayed as a reference image. Then, it is expected that this operation supports the paracentesis operation of the paracentesis needle into the lesion.

Patent Document 1: JP No. 2000-60853 A

DISCLOSURE OF INVENTION

However, in order to capture the elasticity image, it is necessary to iteratively perform operation for compressing a region of interest of a subject with an ultrasound probe and operation for decompressing it. Therefore, the paracentesis operation for invading the paracentesis needle into the living body while measuring the elasticity image has such a danger that the paracentesis needle can damage the body tissue and the paracentesis operation cannot be thus executed while measuring the elasticity image.

On the other hand, in the case of diagnosis with the body tissue having a motion as a region of interest, a tomographic image indicating the organ shape is set as a reference image and the elasticity image is superposed to the reference image and the resultant image is displayed. However, in the comparative observation of both the images, the both images change in accordance with the motion of the organ motion and this can be an obstacle against proper diagnosis.

Then, it is an object of the present invention to provide an ultrasound diagnostic apparatus that can display the elasticity image and the tomographic image in a display format suitable to diagnosis.

In order to solve the problem, an ultrasound diagnostic apparatus according to the present invention comprises: an ultrasound probe that iteratively transmits ultrasonic waves to a subject at time intervals, and receives reflection echo signals on time series corresponding to the iterative transmission of the ultrasonic waves; a receiving-signal processing unit that processes the reflection echo signal received by the ultrasound probe; a tomographic image constructing unit that forms tomographic images on time series on the basis of the reflection echo signal; an elasticity image constructing unit that obtains the displacement of the body tissue of the subject, caused by pressure applied to the subject, on the basis of the reflection echo signal, further obtains the elasticity of parts in the body tissue on the basis of the obtained displacement, and forms elasticity images on time series; a superimposition-image forming unit that forms a superimposition image of the tomographic image and the elasticity image on time series; an input unit that inputs an instruction for controlling the formation of the superimposition image; and a display unit that displays the superimposition image. The ultrasound diagnostic apparatus further comprises: a freezing control portion that inputs a freezing instruction for freezing the display operation on time series of any of the tomographic image and the elasticity image to the input unit, and outputs an image selected on the basis of the freezing instruction, as the frozen image, to the superimposition-image forming unit.

That is, the time-series display operation of any of the tomographic image and the elasticity image is frozen, thereby providing an image in the display format suitable to the diagnosis. For example, in the paracentesis operation, the pressurization to the subject stops and a freezing instruction of the elasticity image is input, and the paracentesis operation can be precisely performed while checking the region of interest with the frozen elasticity image superposed to the tomographic image and displayed. In other words, the relatively positional relationship between the ultrasound probe and the advance/return position of the invasion device attached to the ultrasound probe is generally fixed. Therefore, a doctor as an operator of the invasion device can easily specify the lesion as the paracentesis target on the basis of the frozen elasticity image that is superposed to the tomographic image captured by the ultrasound probe operated by himself/herself and that is thus displayed. As a consequence, the pressurization to the subject stops and the paracentesis operation can be then performed. It is possible to prevent such a danger that the invasion device damages the body tissue and to reduce the number of paracentesis time and reduce the strain of the patient. Incidentally, the advance/return position of the invasion device on the tomographic image can be obtained with calculation. The advance/return position of the invasion device on the superposed image can be displayed as guide, as needed.

On the other hand, upon diagnosing the body tissue (e.g., blood vessel) having a motion and the organ around the tissue as the region of interest, the freezing instruction of the tomographic image is input. Then, with the frozen tomographic image, the elasticity image changing on time series can be observed while referring to the structure and position of the region of interest. This operation can contribute to proper diagnosis.

Herein, the freezing instruction can be input by an operator at the start time of the operation of invasion device. Further, the freezing control portion can be structured to stop the output of the frozen elasticity image in response to a freezing reset instruction to be input and output the elasticity images on time series to the superimposed image forming section. As a consequence, the operator inputs the freezing reset instruction, thereby immediately displaying the elasticity images as real-time images on time series and the correspondence to operation for changing the paracentesis portion is possible.

Further, in the ultrasound diagnostic apparatus according to the present invention, the freezing control portion selects the frozen image from among the images on time series whose display operation on time series is frozen on the basis of the freezing instruction, and outputs the selected frozen image to the superimposition-image forming unit, and the superimposition-image forming unit forms the superimposition image on time series of the frozen image and the image that is displayed on time series.

Furthermore, an elasticity image freezing instruction for freezing the display operation on time series of the elasticity images is input to the input unit, the freezing control portion selects the frozen elasticity image from the elasticity image on time series on the basis of the elasticity image freezing instruction, and outputs the selected image to the superimposition-image forming unit, and the superimposition-image forming unit forms the superimposition image on time series of the frozen elasticity image and the tomographic image on time series.

Alternatively, a tomographic image freezing instruction for freezing the display operation on time series of the tomographic image is input to the input unit. The freezing control portion selects the frozen tomographic image from the tomographic images on time series on the basis of the tomographic image freezing instruction, and outputs the selected image to the superimposition-image forming unit. The superimposition-image forming unit forms the superimposition image on time series of the frozen tomographic image and the elasticity image on time series.

In addition, the input unit comprises input means (e.g., a keyboard or track ball) that inputs the elasticity image freezing instruction.

In addition, the ultrasound probe comprises a jig to which an invasion device is attached. The jig has an advance/return detecting sensor that detects the advance/return of the invasion device to the subject. An advance signal of the invasion device, output from the advance/return detecting sensor, is input to the input unit as the elasticity image freezing instruction.

In addition, the ultrasound probe comprises: a magnetic sensor that detects the position and attitude of the ultrasound probe in cooperation with the three-dimensional magnetic field generated around the subject; and an ultrasound probe movement detecting portion that detects the movement of the ultrasound probe on the basis of a detection signal of the magnetic sensor. A signal indicating that the movement of the ultrasound probe output from the ultrasound probe movement detecting portion is not more than a setting threshold is input to the input unit, as the elasticity image freezing instruction.

In addition, the ultrasound probe comprises a pressure sensor that detects pressure applied to the subject. The ultrasound diagnostic apparatus comprises a pressure measuring portion that receives a pressure signal from the pressure sensor and measures the pressure. A signal indicating the time change of the pressure output from the pressure measuring portion is not more than a setting threshold is input to the input unit, as the elasticity image freezing instruction.

Upon using, as the elasticity image freezing instruction, the signal indicating the state in which the amount of movement of the ultrasound probe or the pressure applied to the subject is not more than the threshold, the display unit displays a body mark indicating the portion of the subject, for obtaining the elasticity image, and a probe mark indicating the arrangement position of the ultrasound probe on the body mark. The freezing control portion controls the setting threshold in accordance with the type of the body mark and the arrangement position of the probe mark. In place of this, or together with this, the freezing control portion controls the setting threshold in accordance with information on the subject.

Further, the freezing control portion selects, as the frozen elasticity image, the elasticity image at the time for inputting the freezing instruction from the elasticity images on time series, and outputs the selected image to the superimposition-image forming unit.

Furthermore, the elasticity image forming unit comprises a frame memory that stores a plurality of the elasticity images from the elasticity image on time series. The display unit displays at least one of the plurality of elasticity images stored in the frame memory. The input unit comprises means that selects a desired one from at least one of the displayed elasticity images. The freezing control portion outputs the selected desired elasticity image as the frozen elasticity image to the superimposition-image forming unit.

In addition, the input unit inputs a freezing reset instruction for resetting the freezing operation displayed on time series. In this case, the freezing control portion outputs the images on time series whose display operation on time series is frozen to the superimposition-image forming unit on the basis of the freezing reset instruction.

The ultrasound diagnostic apparatus according to the present invention further comprises an amount-of-movement calculating section that calculates the amount of movement of the tomographic image after inputting the freezing instruction from the tomographic image from the time for inputting the freezing instruction. The superimposition-image forming unit moves the position of the frozen elasticity image to match the position of the tomographic image after the freezing instruction by using the amount of movement. In place of this, or together with this, the superimposition-image forming unit outputs a warning message (e.g., warning display operation or warning sound) indicating the amount of movement is over a setting threshold.

Further, the ultrasound probe is a hybrid ultrasound probe comprising a cylindrical basic portion that can be inserted in the body cavity of the subject, and an ultrasound probe for transverse section having arrangement of a plurality of ultrasound vibrators in the direction parallel with the tomographic surface and an ultrasound probe for longitudinal section having arrangement of a plurality of ultrasound vibrators in the direction orthogonal to the tomographic surface at the end of the basic portion. In this case, the jig to which the invasion device is attached supports the invasion device to be capable of advance and return in the direction orthogonal to an ultrasound emission surface of the ultrasound probe for transverse section. The tomographic image constructing unit forms a lateral tomographic image on the basis of the reflection echo signal corresponding to the ultrasound probe for transverse section, and further forms a longitudinal tomographic image on the basis of the reflection echo signal corresponding to the ultrasound probe for longitudinal section. The elasticity image constructing unit forms the elasticity image on the basis of the reflection echo signal corresponding to the ultrasound probe for transverse section. Thus, the ultrasound probe for longitudinal section captures the image of the invasion device, and the invasion device is displayed on the longitudinal tomographic image. As a consequence, the operation operates the invasion device while directly observing the advance position of the invasion device and can sample a desired organ cell of the lesion.

Further, the invasion device position calculating section detects the advance/return position of the invasion device on a longitudinal tomographic image, the invasion device forms guide display indicating the advance/return position on a lateral tomographic image, and the guide display is displayed on the lateral tornographic image. As a consequence, the operator only observes the lateral tomographic image to which the elasticity image is superposed and displayed, thereby directly observing the advance position of the invasion device with images. The operation of the invasion device is further simple, and a desired organ cell of the lesion can be sampled without fail.

BRIEF DESCRIPTION OF THE DRAWINGS

FIG. 9 is a block diagram showing the structure of an ultrasound diagnostic apparatus according to the third embodiment of the present invention.

BEST MODE FOR CARRYING OUT THE INVENTION

Hereinbelow, a description will be given of ultrasound diagnostic apparatuses according to embodiments of the present invention with reference to the drawings.

First Embodiment

Figure 1:
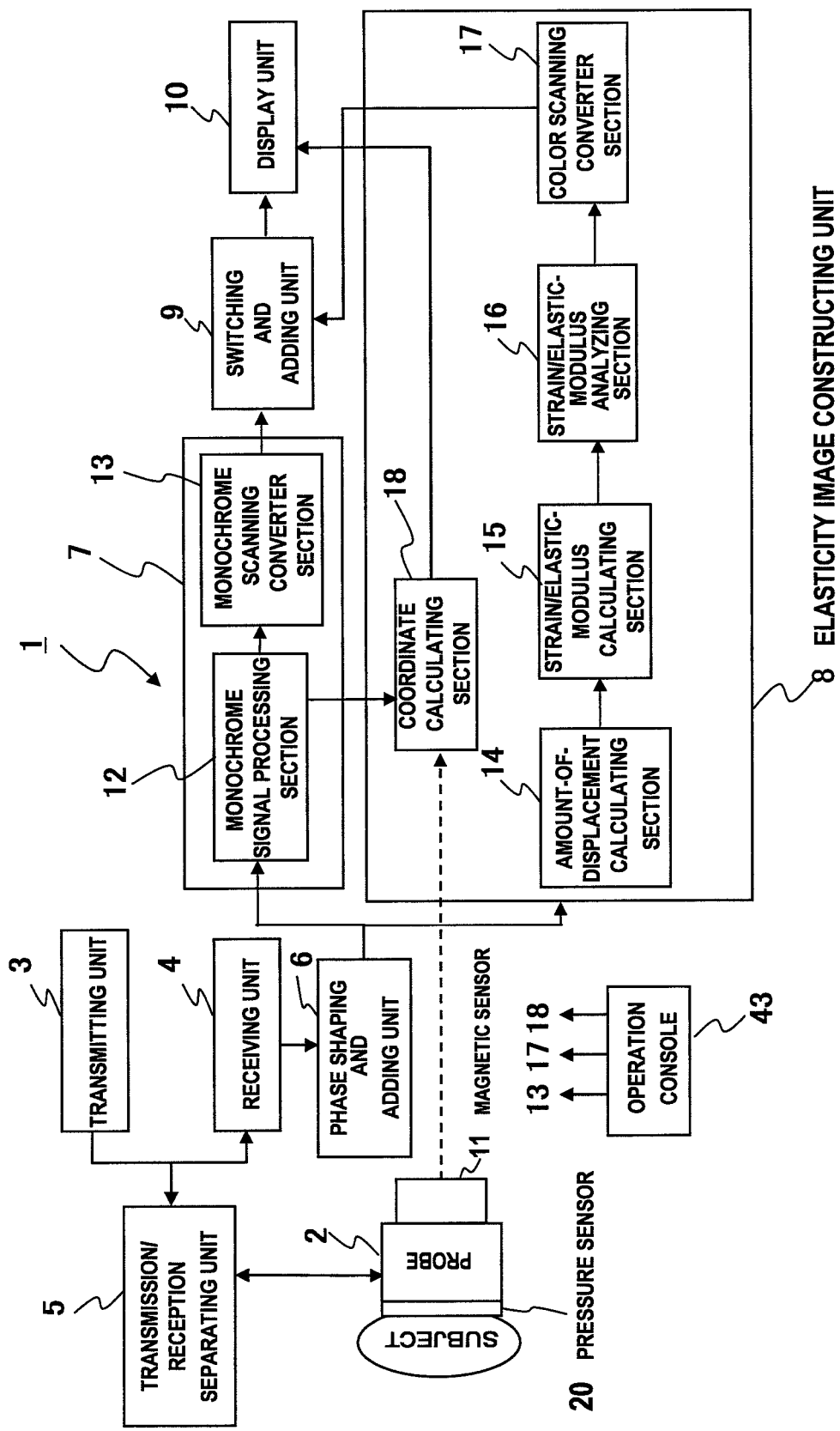
FIG. 1 is a block diagram showing the structure of an ultrasound diagnostic apparatus according to the first embodiment of the present invention.

FIG. 1 is a block diagram showing an ultrasound diagnostic apparatus 1 according to the first embodiment of the present invention. Referring to FIG. 1, an ultrasound probe (hereinafter, referred to as a probe) 2 iteratively transmits ultrasonic waves to a subject at time intervals, and receives reflection echo signals on time series corresponding to the iterative transmission of the ultrasonic waves. Although not shown, the probe 2 has arrangement of a plurality of vibrators, and further has a function for electrically scanning the plurality of vibrators, performing ultrasound beam scanning to a predetermined tomographic surface of the subject, and receiving the reflection echo signals from the subject in accordance with the ultrasound beam scanning. Incidentally, as the probe 2, e.g., a bodysurface-type probe used for coming into contact with the body surface of the subject and a transrectal-type probe used for being inserted into the body cavity can be applied. Further, the probe 2 has a magnetic sensor 11 for measuring the position and attitude of the probe 2 in cooperation with the three-dimensional magnetic field formed around the subject.

Figure 2:
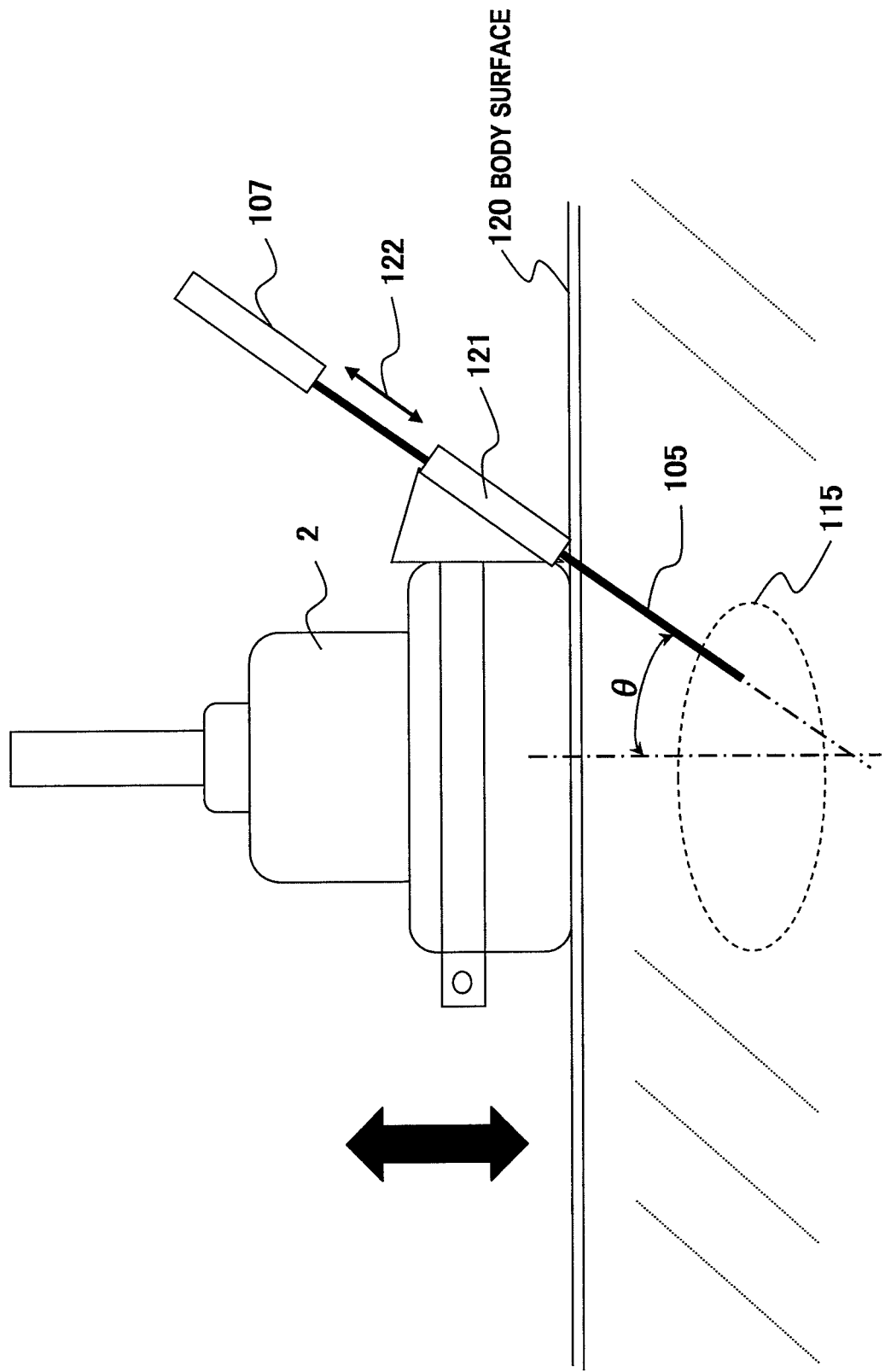
FIG. 2 is a diagram for illustrating the structure of one example of a probe.

FIG. 2 shows an example of the probe 2 according to the first embodiment. Referring to FIG. 2, the probe 2 according to the first embodiment comes into contact with a body surface 120, thereby being used. For example, a tomographic image and an elasticity image of the body surface of the mammary gland, thyroid, abdomen, etc. are captured and are used for sampling the organ of the lesion. An adapter 121 as a jig for supporting a paracentesis needle 105 is attached to the probe 2. The adapter 121 supports the paracentesis needle 105 to be capable of advancing and returning in the direction shown by an arrow 122. Further, the adapter 121 is attached so that the advancing and returning position of the paracentesis needle 105 matches the position of the ultrasound scanning surface of the probe 2 and the advancing and returning direction of the paracentesis needle 105 is inclined at an angle θ to the central axis of the ultrasound scanning surface of the probe 2. In this case, since the advancing and returning surface of the paracentesis needle 105 is included in the ultrasound scanning surface, an image of the paracentesis needle 105 is drawn to the tomographic image. Further, a dispenser 107 arranged to the rear end of the paracentesis needle 105 is operated, thereby invading the paracentesis needle 105 into the subject. Further, the adapter 121 has a mechanism for varying the angle θ of the advancing and returning direction of the paracentesis needle 105 at a plurality of setting steps. Furthermore, referring also to FIG. 2, reference numeral 115 denotes the lesion as an example.

A transmitting unit 3 drives the probe 2 and generates a transmitting pulse signal for transmitting the ultrasonic waves. Further, the transmitting unit 3 has a function for setting a convergence point of the ultrasonic waves sent from the probe 2 to an arbitrary depth of the subject. A receiving unit 4 receives the reflection echo signal from the subject, received by the probe 2, and performs signal processing such as amplification with predetermined gain. Further, a transmission/reception separating unit 5 transmits the transmuting pulse signal from the transmitting unit 3 to the probe 2, and further transmits the reflection echo signal from the probe 2 to the receiving unit 4 by switching a signal line. A phase shaping and adding unit 6 inputs an echo signal subjected to receiving processing by the receiving unit 4, controls the phase, and shapes the phase and adds the phases, thereby transmitting converged ultrasound beams to a plurality of convergence points to form RF-signal frame data on time series. The receiving unit 4 and phase shaping and adding unit 6 form a receiving-signal processing portion for forming RF frame data on time series corresponding to the tomographic surface of the subject.

A tomographic image constructing unit 7 restructures a grayscale tomographic image (e.g., monochrome tomographic image) of the subject on the basis of the RF-signal frame data output from the phase shaping and adding unit 6. An elasticity image constructing unit 8 obtains the displacement of the body tissue in the subject, due to the increase/decrease in pressure applied to the subject on the basis of the RF-signal frame data output from the phase shaping and adding unit 6, and obtains the elasticity of parts in the body tissue on the basis of the obtained displacement and forms a color elasticity image on time series. The grayscale tomographic image and color elasticity image restructured by the tomographic image constructing unit 7 and the elasticity image constructing unit 8 are input to a switching and adding unit 9. Further, the tomographic image constructing unit 7 and the elasticity image constructing unit 8 individually have a freezing control portion for outputting an image selected on the basis of a freezing instruction input from an operation console 43 forming an input unit, as the frozen image, to the switching and adding unit 9. The operation console 43 is an input unit for performing various setting and operation by a user.

The switching and adding unit 9 has a superimposition image forming portion for forming an image displayed on a display unit 10. That is, the switching and adding unit 9 has a function for displaying any of the grayscale tomographic image and the color elasticity image to the display unit 10 in accordance with the input instruction, a function for arranging and displaying the grayscale tomographic image and color elasticity image on the display unit 10, and a function for allowing the display unit 10 to display a superimposition image obtained by adding the grayscale tomographic image and the color elasticity image. The display unit 10 displays display image data output from the switching and adding unit 9, as an image. Although not shown in FIG. 1, the display unit 10 has a system control portion for entirely controlling the ultrasound diagnostic apparatus 1.

Herein, a description will be given of the detailed structure of the tomographic image constructing unit 7 and the elasticity image constructing unit 8. The tomographic image constructing unit 7 comprises a monochrome signal processing section 12 and a monochrome scanning converter section 13. The monochrome signal processing section 12 inputs the RF-signal frame data from the phase shaping and adding unit 6, performs signal processing including gain correction, log compression, detection, contour emphasis, and filter processing, and thus obtains tomographic image data. Further, although not shown, the monochrome scanning converter section 13 includes an A/D converter that converts the tomographic image data from the monochrome signal processing section 12 into a digital signal, a frame memory that stores a plurality of pieces of converted tomographic image data on time series, and a controller. Furthermore, the monochrome scanning converter section 13 reads the tomographic image frame data stored in the frame memory as one image with the controller synchronously with TV, and outputs the resultant data to the switching and adding unit 9. Moreover, the monochrome scanning converter section 13 has a freezing control portion that outputs, to the switching and adding unit 9, the image selected by the freezing instruction input from the operation console 43 as the frozen image.

The elasticity image constructing unit 8 comprises: an amount-of-displacement calculating section 14; a strain/elastic-modulus calculating section 15; a strain/elastic-modulus analyzing section 16; a color scanning converter section 17; and a coordinate calculating section 18. In addition, the elasticity image constructing unit 8 includes a pressure measuring portion that measures pressure applied to pressure with the probe 2.

The amount-of-displacement calculating section 14 includes an RF-signal frame data selecting portion and a calculating portion, selects one set of the RF-signal frame data at different measurement time on the basis of the RF-signal frame data output from the phase shaping and adding unit 6, and obtains the displacement of the body tissue. That is, the RF-signal frame data selecting portion includes a frame memory and a selecting portion, stores a plurality of pieces of the RF-signal frame data from the phase shaping and adding unit 6 to the frame memory, and selects one set of the stored RF-signal frame data, i.e., two pieces of the RF-signal frame data with the selecting portion. For example, the RF-signal frame data selecting portion captures the RF-signal frame data on time series on the basis of a frame rate of the image by the phase shaping and adding unit 6, and sequentially stores the selected data to the frame memory. Further, the selecting section selects, as first data, the current-captured RF-signal frame data (n) in accordance with the instruction from the system control portion, and moreover selects one piece of the RF-signal frame data (x) from the RF-signal frame data (n+1, n+2, n+3, n+m) to be captured in future. That is, referring to FIG. 3, the selecting portion selects, e.g., the current-captured (n+1-th RF-signal frame data and the next-captured (n+2)-th RF-signal frame data. Incidentally, reference numerals n, m, and x denote index numbers added to the RF-signal frame data that are natural numbers.

Figure 3:
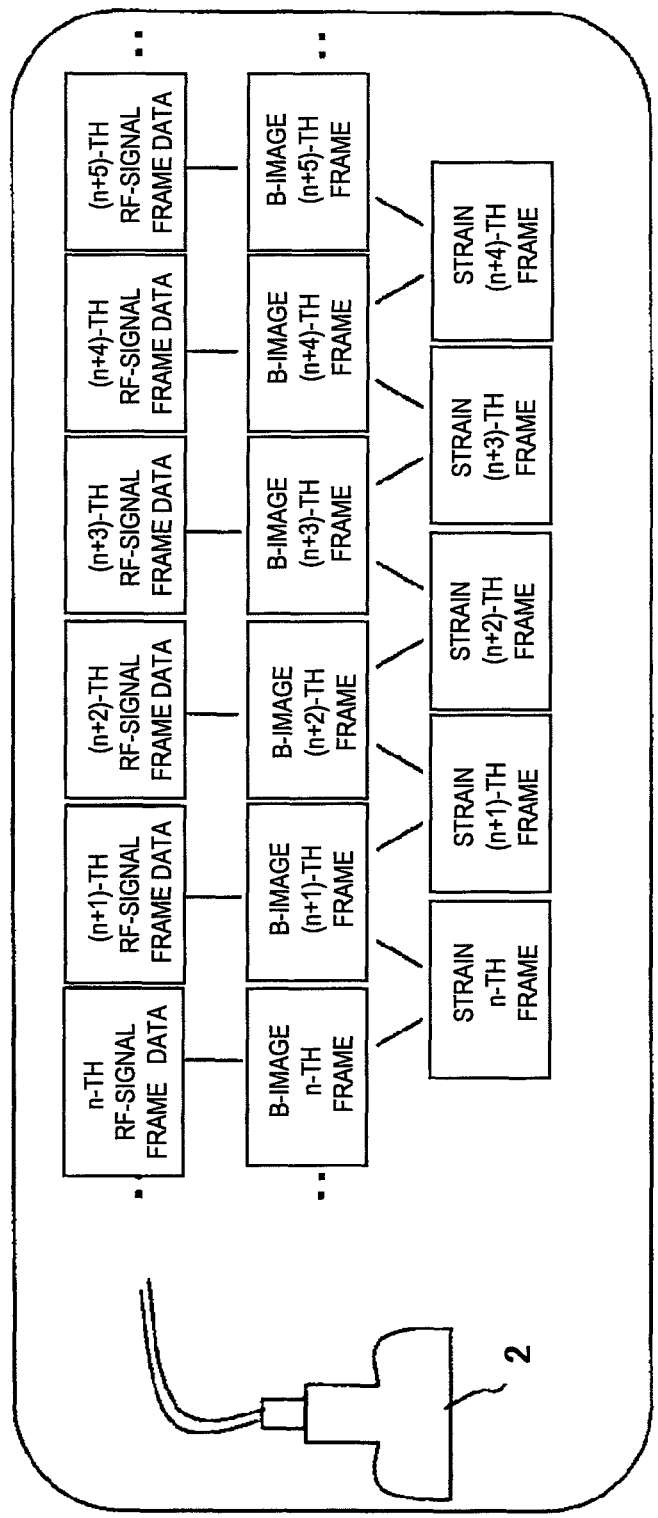
FIG. 3 is a diagram for illustrating an example of calculating the displacement in an amount-of-displacement calculating section.

Then, the calculating portion calculates the displacement of the body tissue on the basis of the selected one set of the RF-signal frame data (n, x). For example, as shown in FIG. 3, upon transferring one set of the RF-signal frame data (n, n+1), the calculating portion sets the RF-signal frame data (n, n+1) as B-mode image frames (n, n+1), performs one-dimensional or two-dimensional correlation processing from the two frames, obtains the one-dimensional or two-dimensional displacement distribution of the displacement at the body tissue corresponding to points on the tomographic image, and thus forms strain frame data n. In place of the displacement, a moving vector (direction and size of the displacement) of the body tissue can be obtained. The detection of the moving vector can use a well-known block matching method. According to the block matching method, the image is divided into blocks having N×N pixels, attention is paid to the block within a region of interest, the block that is the most approximate to the target block is searched from the previous frames, and the moving direction and size of the block are obtained and are set as the moving vector in the center within the region of interest.

The strain/elastic-modulus calculating section 15 calculates the strain of the body tissue on the basis of the displacement (e.g., moving vector) calculated by the amount-of-displacement calculating section 14, and forms elasticity image frame data of the elasticity image on the basis of the strain. The strain is calculated by spatially differentiating the displacement of the body tissue. On the other hand, the elastic modulus is calculated by dividing the change in the pressure operating the parts of the target organ by the change in the displacement. For example, $\Delta L$ denotes the displacement calculated by the amount-of-displacement calculating section 14, and $\Delta P$ denotes the pressure operating the parts of the target organ. Strain S can be calculated by spatially differentiating $\Delta L$. Therefore, the strain S can be obtained by using an expression of $S=\Delta L/X$. Incidentally, x denotes the distance in the differentiating direction. Further, the Young's modulus Ym serving as the Young's modulus Ym of the most basic (one-dimensional) model is calculated by an expression of $Ym=\Delta P/S(\Delta P)/(\Delta L/X)$. With the Young's modulus Ym, the elastic modulus of the body tissue corresponding to points of the tomographic image is calculated. As a consequence, two-dimensional elasticity image data can be continuously obtained.

Herein, in order to obtain the elastic modulus, as mentioned above, it is necessary to obtain the pressure applied to the parts of the body tissue. The well-known methods variously-proposed can be applied to a measurement method of the pressure. According to the first embodiment, although not shown, and the strain/elastic-modulus calculating section 15 has a pressure measuring portion that attaches a pressure sensor to the probe 2 used to come into contact with the body surface of the subject, which detects the pressure applied to the body surface of the subject by the probe 2, and that estimates pressure (stress) applied to the parts of the body tissue of the subject on the basis of the detected pressure.

Figure 4:
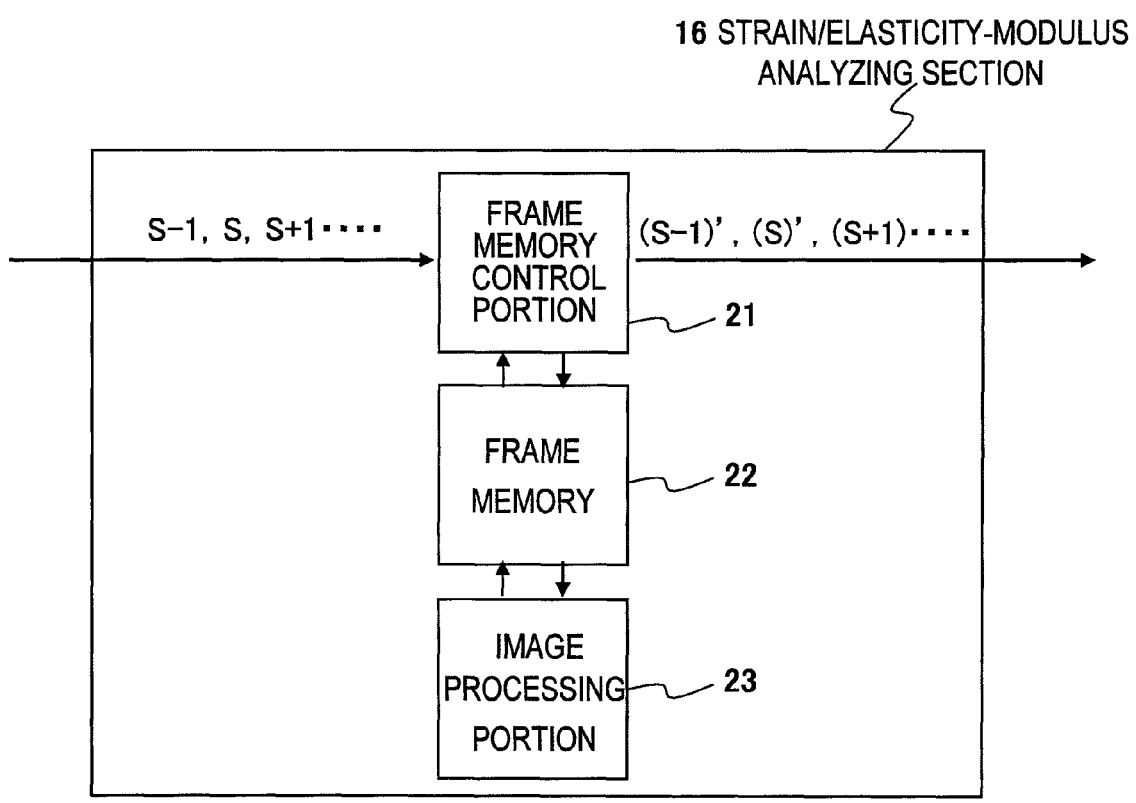
FIG. 4 is a block diagram showing the structure of a strain/elastic-modulus analyzing section.

Referring to FIG. 4, the strain/elastic-modulus analyzing section 16 comprises a frame memory control portion 21, a frame memory 22 that stores a plurality of pieces of frame data, and an image processing portion 23. The image processing portion 23 performs predetermined image processing of the elasticity image frame data stored in the frame memory 22. As the mage processing, e.g., it is possible to properly use frame data selecting processing, adding processing for stabilization that displays data for stabilization, threshold processing, grayscale processing, and comparing processing after the grayscale processing. The frame memory control portion 21 performs processing writing, to the frame memory 22, the elasticity image frame data output from the strain/elastic-modulus calculating section 15 and processing for reading the elasticity image frame data from the frame memory 22 and outputting the read data to the color scanning converter 17. Further, the frame memory control portion 21 controls the frame memory 22 upon performing various signal processing by the image processing portion 23 and the frame memory 22.

The color scanning converter section 17 converts the analyzed elasticity image frame data, output from the strain/elastic-modulus analyzing section 16, and hue information to the converted data. That is, referring to FIG. 5, the color scanning converter section 17 comprises a frame memory 29, an RGB data memory 30 that stores hue information data, and a memory control portion 31. That is, red (R), green (G), and blue (B) serving as light's three primary colors are added to the analyzed elasticity image frame data. For example, the elasticity data with large strain is converted into a red code, and the elasticity data with small strain is converted into a blue code.

The switching and adding unit 9 constitutes the superimposition-image forming unit according to the first embodiment. That is, the switching and adding unit 9 stores the monochrome tomographic image data from the monochrome scanning converter section 13 and the elasticity image data from the color scanning converter section 17 into the memory, and adds and combines the tomographic image data and elasticity image data at a setting ratio in accordance with the instruction from the system control portion, thereby forming a display image. Brightness information and hue information of pixels on the combined display image are obtained by adding, at the setting ratio, the information of the monochrome tomographic image and the color elasticity image. Further, the switching and adding unit 9 selects the image displayed on the display unit 10 from among the tomographic image data and elasticity image data and the combined display image data in accordance with the instruction from the system control section.

Herein, a description will be given of the operation of the ultrasound diagnostic apparatus 1 with the above-mentioned structure. In the ultrasound diagnostic apparatus 1, the transmitting unit 3 iteratively transmits ultrasonic waves to the subject via the probe 2 that comes into contact with the subject at the time intervals, the receiving unit 4 receives the reflection echo signals on time series, generated from the subject, and the phase shaping and adding unit 6 shapes the phase and adds the phases, thereby forming RF-signal frame data. Then, the tomographic image constructing unit 7 converts the RF-signal frame data into the monochrome tomographic image and stores the resultant data to the frame memory. The monochrome tomographic image stored in the frame memory is read synchronously with TV, thereby displaying the resultant data on the display unit 10 via the switching and adding unit 9. On the other hand, the elasticity image constructing unit 8 forms a color elasticity image on the basis of the RF-signal frame data output from the phase shaping and adding unit 6. The switching and adding unit 9 adds the above-obtained monochrome tomographic image and color elasticity image, and forms the combined display image, thereby displaying the resultant data on the display unit 10. Herein, the switching and adding unit 9 cannot combine the tomographic image data and the elasticity image data in accordance with the instruction of the system control portion, and can individually display the resultant data on the display unit 10.

Next, a description will be given of an example of processing of the strain/elastic-modulus analyzing section 16 and the color scanning converter section 17. According to the first embodiment, input means such as the operation console 43 inputs a region ROI of interest for obtaining elasticity data via the system control portion, sets the region ROI of interest to the tomographic image, and obtains the elasticity image data of only the region ROI of interest.

First, referring to FIG. 4, the frame memory control portion 21 in the strain/elastic-modulus analyzing section 16 captures the strain data calculated by the strain/elastic-modulus calculating section 15, as the elasticity image frame data, on time series (S−1, S, S+1 . . . ) on the basis of frame unit, and stores the resultant data to the frame memory 22 in the analysis section. Then, the image processing portion 23 undergoes the elasticity image frame data stored in the frame memory 22 to the image processing including frame data selecting processing, adding processing for stabilization for display operation for stabilization, threshold processing, grayscale processing, and comparing processing after the grayscale processing. The frame data selecting processing is performed to delete the strain frame data that does not reach the setting value from among the elasticity image frame data obtained in the continuous pressurizing processing and to form an image of only the frame upon applying the proper amount of pressure. Further, the adding processing for stabilization is performed to execute smoothing processing in the time direction of the elasticity image frame data that is calculated and displayed in real time and suppress the sharp change. The grayscale processing is performed to execute statistic processing of the strain in the ROT for displaying the elasticity image on the basis of the strain data calculated by the strain/elastic-modulus calculating section 15, e.g., to calculate an average value Savc of the strain of the body tissue within the ROI. Then, a minimum value 5 min (hard) and a maximum value Smax (soft) of the strain are arbitrarily set on the basis of the average value, the interval between the minimum value and the maximum value is divided into, e.g., 256 grayscales, and values of the strain of the body tissue corresponding to the pixels within the ROI into corresponding grayscales. As mentioned above, the elasticity image frame data having the assigned hue and grayscale is stored to the frame memory 22. Further, the threshold processing is performed to display, with so-called binarization display, the color elasticity image at the region having predetermined hardness on the display unit 10. For example, in the grayscale processing, it is assumed that the minimum value 5 min=average value Savex (A) and the maximum value Smax=average value Savex (B). Further, the range of the threshold Sth is set as Smin<Sth<Save or Save<Sth<Smax, thereby setting a "threshold" having a quantitative value that is "harder" than the average value by X times or is "softer" than the average value by Y times. This threshold can be input and set from the operation console 43 in the system control section. Then, the "threshold" is compared with the strain data of the individual pixels of the elasticity image frame data, and pixel data that is not less than "threshold" or not-less-than the "threshold" is extracted. As a consequence, blue or red can be assigned to the pixel within the region harder than that of the threshold. The elasticity image frame data processed with the threshold is stored to the frame memory 22. Incidentally, it is possible to prevent the threshold processing with the operation of the operation console. The elasticity image frame data subjected to the grayscale processing or the elasticity image frame data subjected to the threshold processing is output, as the analyzed elasticity frame data, to the color scanning converter section 17 on time series ((S−1)', S', (S+1)', . . . ). Incidentally, the above description is given of the case of displaying the color elasticity image only on the region of the body tissue, having predetermined hardness, with the threshold processing. On the other hand, the color elasticity image only on the region having predetermined hardness or less may be displayed. In this case, inequality signs in the relations are reversed.

Next, a description will be given of one example of comparing processing after the grayscale processing by the image processing portion 23. With respect to the elasticity image frame data on time series subjected to the grayscale processing, the pixel data of the current-measured elasticity image frame data is compared with the pixel data of the previously-measured elasticity image frame data. The pixel data having the difference smaller than a setting value is determined as that having the amount of pressure applied by the probe 2. The pixel data having the difference larger than the setting value is determined as that having the changed amount of pressure. On the basis of the determination, only the elasticity image frame data to be transferred to the color scanning converter section 17, corresponding to the pixel portion having the changed value can be updated. Incidentally, the comparing processing after the grayscale processing can be omitted with by the operation of the operation console 43.

Figure 5:
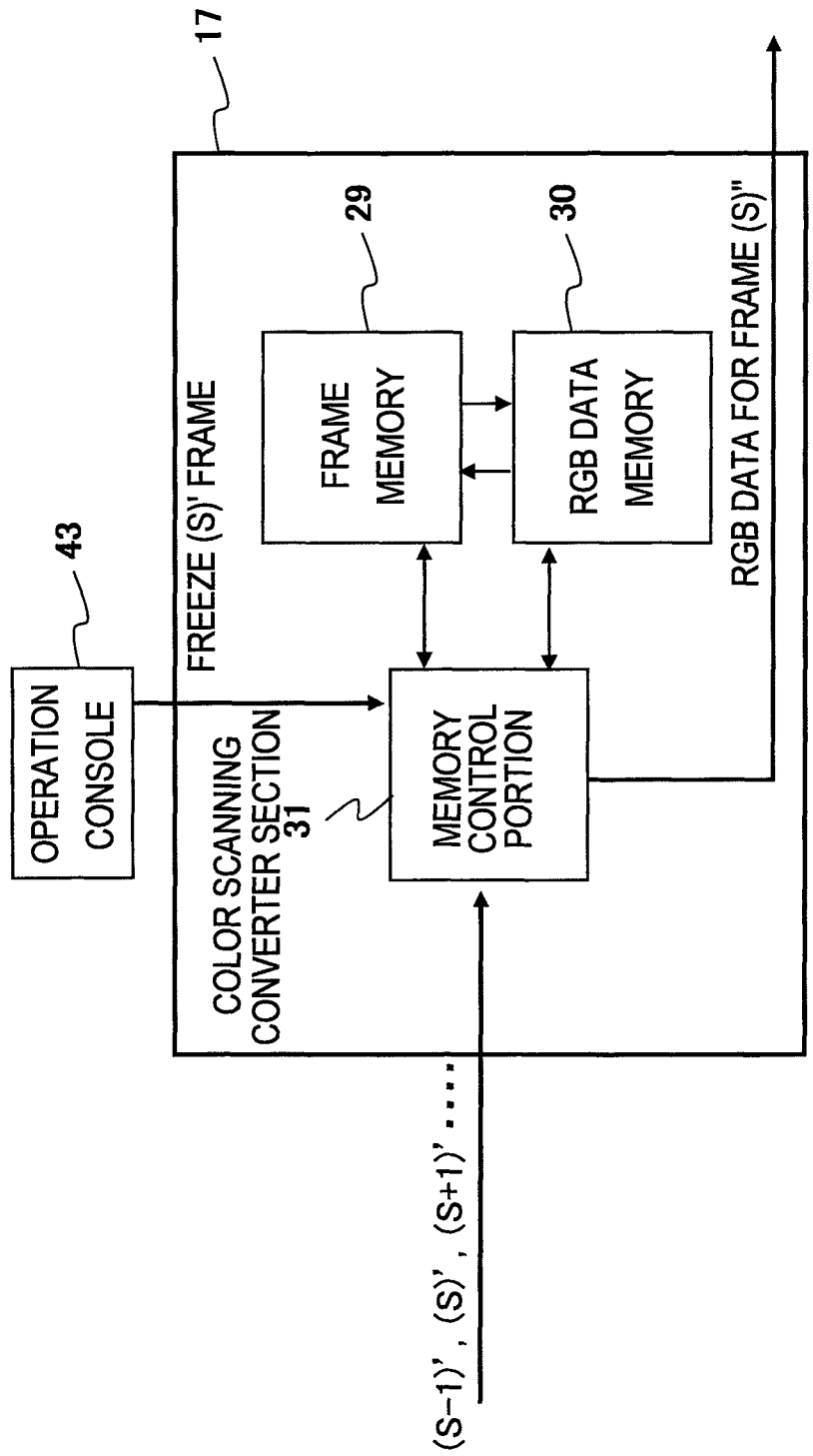
FIG. 5 is a block diagram showing the structure of a color scanner converter.

Next, a description will be given of one example of the processing of the color scanning converter section 17 in accordance with FIG. 5. The analyzed elasticity image frame data output from the strain/elastic-modulus analyzing section 16 is stored to the frame memory 29 by a write signal from the memory control portion 31. The RGB data memory 30 previously stores the hue information data (R-, G-, and B-values). The memory control portion 31 reads the analyzed elasticity image frame data in the elasticity image frame data and the hue information in the RGB data memory 30, and structures the color elasticity image. That is, the color scanning converter section 17 reads the hue information in the RGB data memory 30 corresponding to a value of the elasticity image frame data in the frame memory 29, and adds the hue information to the elasticity image frame data. The memory control portion 31 outputs the color elasticity image to the switching and adding unit 9.

Herein, a description will be given of the freezing operation of the elasticity image in the operation of an invasion device as the feature of the present invention. When the operator starts the operation of the invasion device, referring to FIG. 5, a freezing instruction of the elasticity image input to the memory control portion 31 in the color scanning converter section 17 is input from the operation console 43 provided for the system control section. The memory control portion 31 comprises a function of a freezing control portion according to the present invention. When the freezing instruction is input in the case of elasticity image frame data of an (S)'-th frame, the memory control portion 31 stops the operation for writing the elasticity image frame data of the next frame, output from the strain/elastic-modulus analyzing section 16, to the frame memory 29. As a consequence, even if inputting the analyzed elasticity image frame data from the strain/elastic-modulus analyzing section 16, the operation for writing the analyzed elasticity image frame data of an (S+1)'-th frame and subsequent frames to the frame memory 29 is not performed. Then, the memory control portion 31 reads the elasticity image frame data of the (5)'-th frame in the frame memory 29 and adds the hue information every time when the strain/elastic-modulus analyzing section 16 inputs the analyzed elasticity image frame data of the (S+1)'-th frame and subsequent frames, serving as subsequent frames of the (5)'-frame, and outputs the color elasticity image of an (S)"-th frame to the switching and adding unit 9. Incidentally, the operation for writing the elasticity image frame data of a plurality of frames to the frame memory 29 is possible, one of the freezing instructions input from the operation console 43 can be selected, and the elasticity image frame data can be output, as the frozen image, to the switching and adding unit 9.

Figure 6:
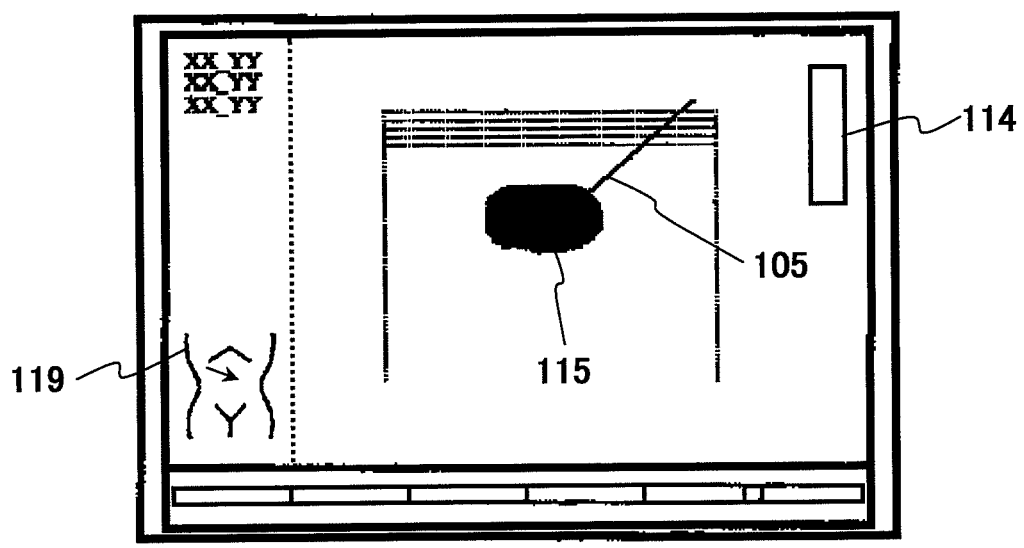
FIG. 6 is a diagram showing an image display example according to the first embodiment.

The tomographic image output from the monochrome scanning converter section 13 as mentioned above and the color elasticity image output from the color scanning converter section 17 are superposed by the switching and adding unit 9. The formed superposed image is displayed on the display unit 10. An example of the superimposition image will be shown in FIG. 6. According to the first embodiment, referring to FIG. 6, since the paracentesis needle 105 is represented on the tomographic image, it is possible visibly check a positional relationship between the paracentesis needle 105 on the tomographic image and the lesion 115 of frozen elasticity image superposed and displayed on the tomographic image at a glance. If the advancing direction of the paracentesis needle 105 is deviated from the paracentesis needle 105 by checking FIG. 6, the adjustment is performed by changing the angle of the paracentesis needle 105. Further, the freezing operation of the elasticity image is reset and the position and angle of the probe 2 are changed so that the paracentesis needle 105 invades into the lesion 115. Thus, the paracentesis operation of the paracentesis needle 105 can be accurately supported. As shown in FIG. 6, reference numeral 114 denotes a color bar indicating a relationship between the level of elasticity and the hue.

According to the first embodiment, when the operator performs the operation of the invasion device, the freezing instruction is input to the color scanning converter section 17 in the elasticity image constructing unit 8 from the operation console 43 and the invasion operation of the paracentesis needle into the living body thereafter starts, thereby preventing a danger that the invasion device such as the paracentesis needle damages the body tissue.

Further, even if stopping the pressurizing operation to the subject, the latest or desired elasticity image is superposed and displayed on the monochrome tomographic image displayed in real time. Therefore, a doctor who operates the invasion device can easily specify the lesion as a paracentesis on the basis of the elasticity image superposed and displayed on the tomographic image captured by the ultrasound probe operated by himself/herself. As a consequence, the paracentesis of the invasion device such as the paracentesis needle to the lesion is possible on the basis of a relatively positional relationship between the invasion device and the ultrasound probe.

Further, upon resetting the freezing instruction input from the operation console, the memory control portion 31 stops the output of the frozen elasticity image in response to the instruction, and outputs the elasticity image on time series stored in the cinema memory 30 to the color scanning converter section 17 serving as a display image forming section. As a consequence, the operator resets the freezing instruction, thereby immediately displaying the elasticity image on time series as a realtime image. Therefore, the predetermined can correspond to that for changing the paracentesis portion.

Further, the display unit 10 displays the color elasticity image of the portion having predetermined hardness, thereby grasping the hardened portion of the organ having suspicion of cancer at a glance. The paracentesis portion can be easily specified.

Although not shown in FIG. 2, a jig 106 that supports the paracentesis needle 105 can have an advance/return detecting sensor that detects the advancing/returning position of the paracentesis needle 105. An advance signal detected by the advance/return detecting sensor, indicating the start of advance of the paracentesis needle 105 is input to the operation console 43, as the freezing instruction. Thus, the elasticity image can be automatically frozen without operating the operation console 43 by the operator and inputting the freezing instruction. Further, as the freezing reset instruction, it is possible to use a return signal indicating the end of the paracentesis needle 105, output from the advance/return detecting sensor.

Second Embodiment

As mentioned according to the first embodiment, even if stopping the pressurization to the subject, the frozen image of the latest or desired elasticity image is superposed and displayed in real time on the monochrome tomographic image. Therefore, a doctor serving as an operator of the invasion device can easily specify the lesion as a paracentesis target by viewing the frozen elasticity image. However, if the time for operating the invasion device is long, the relatively positional relationship between the probe 2 and the subject can be deviated. In this case, since the elasticity image updated in real time is deviated from the frozen elasticity image, there is a danger that the paracentesis operation can be performed to an erroneous position.

Figure 7:
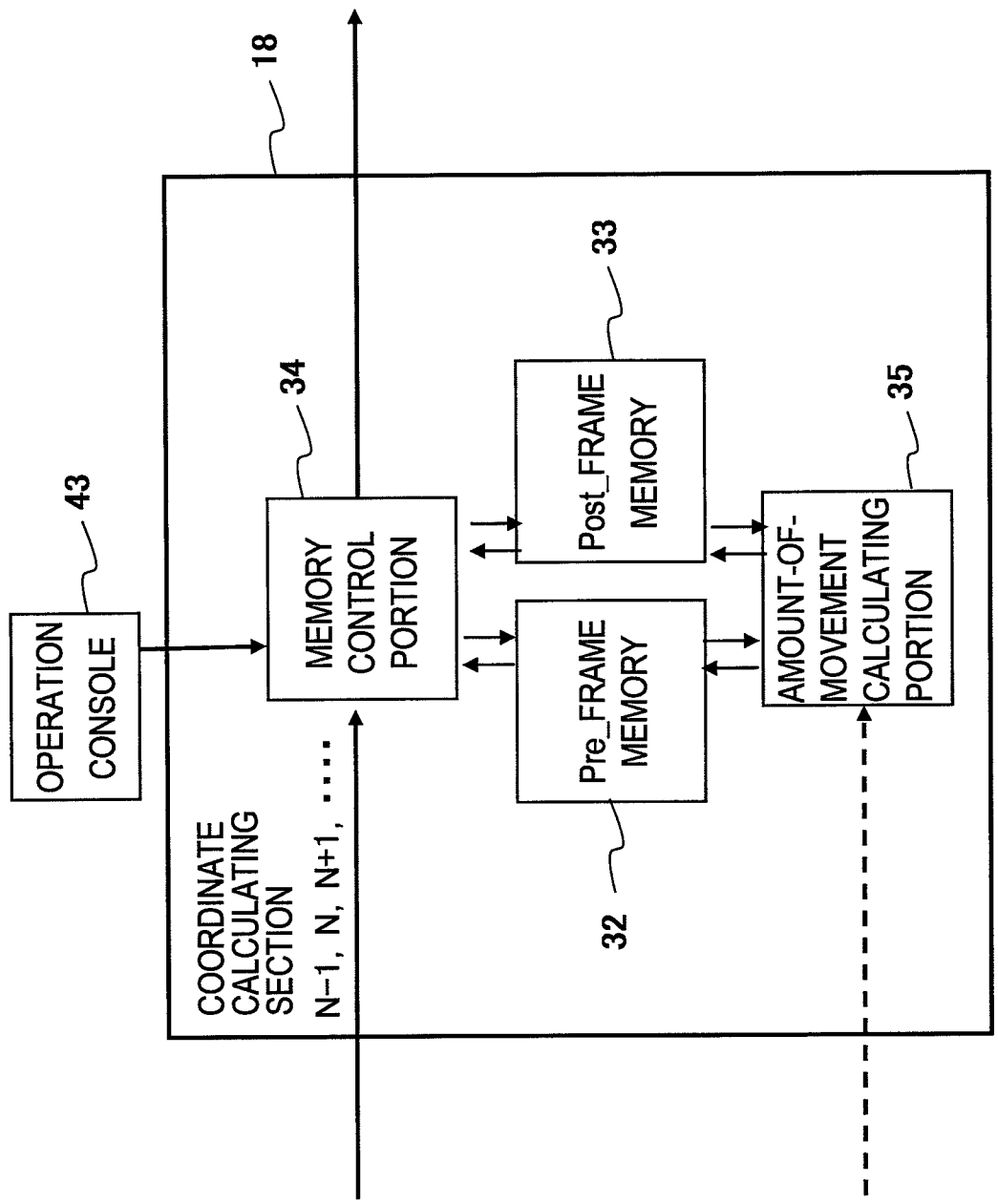
FIG. 7 is a block diagram showing a coordinate calculating section shown in FIG. 1 according to the second embodiment.

Then, according to the second embodiment, with the coordinate calculating section 18 shown in shown in FIG. 1, the position of the frozen elasticity image is corrected by the following operation to the movement of the tomographic image updated in real time. That is, referring to FIG. 7, the coordinate calculating section 18 comprises: a Pre_frame memory 32; a Post_frame memory 33; a frame memory control portion 34 to be controlled; and an amount-of-movement calculating portion 35. The frame memory control portion 34 captures the tomographic image data, upon inputting the freezing instruction, corresponding to the frozen elasticity image from the monochrome signal processing section 12, and stores the captured data to the Pre frame memory 32. Further, frame memory control portion 34 captures the tomographic image data after inputting the freezing instruction from the monochrome signal processing section 12, and stores the captured data to the Post_frame memory 33. The amount-of-movement calculating portion 35 obtains the displacement of the body tissue corresponding to points on the tomographic image by performing the one-dimensional or two-dimensional correlation processing with the toinographic image data corresponding to two frames stored to the Pre frame memory 32 and the Post_frame memory 33. Alternatively, the amount-of-movement calculating portion 35 searches for a block having the most approximate value within a search range on the basis of the brightness value or a value obtained by differentiating the brightness value for the tomographic image data within a specific block with the block matching method, and estimates the amount of movement.

Figure 8A:
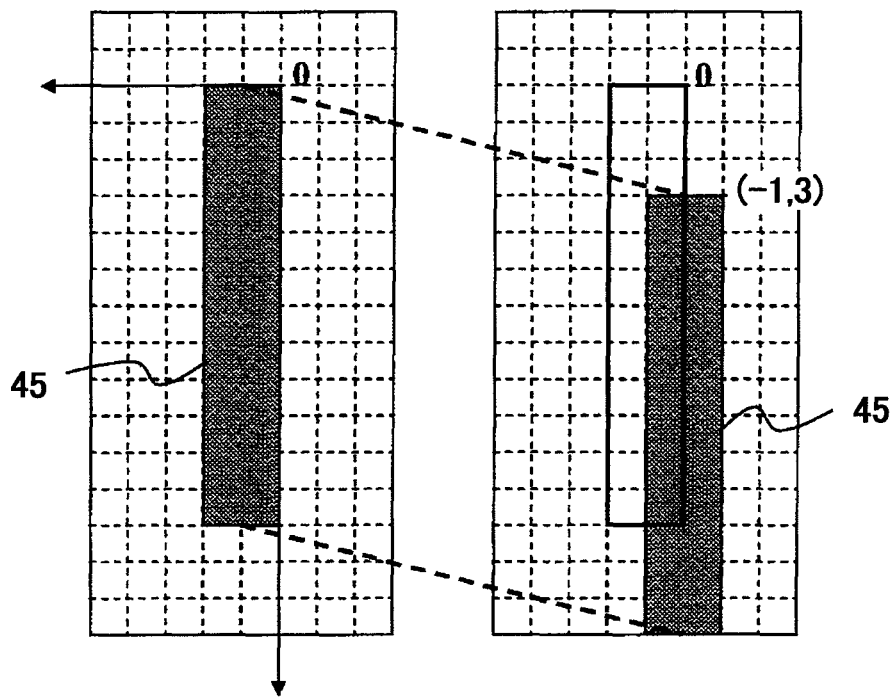
FIG. 8A is a diagram for illustrating a calculating method of the amount of motion of a tomographic image in a coordinate calculating section according to the second embodiment.

Hereinbelow, a description will be given of one example of processing of the coordinate calculating section 18 having the above structure with reference to FIGS. 8A and 8B. Before inputting the freezing instruction from the operation console 43, the frame memory control portion 34 stores the latest tomographic image data from the monochrome signal processing section 12 from the Pre frame memory 32. In this case, no data is stored to the Post_frame memory 33. Further, the frame memory control portion 34 stores the tomographic image data (of, e.g., the (n)-th frame) in the Pre frame memory 32 upon inputting the freezing instruction from the operation console 43, and stores, to the Post_frame memory 33, the tomographic image data of subsequent frames to the (n-th frame (e.g., (n+1-th frame, (n+2)-th frame, The amount-of-movement calculating portion 35 calculates the amount of movement of the probe 2 from the time for inputting the freezing instruction on the basis of the tomographic image data in the Pre frame memory 32, just after stopping the operation for writing the tomographic image data and freezing the operation, and the tomographic image data in the Post_frame memory 33, updated in real time. A description will be given of a calculating method of the amount of movement based on the brightness information of the tomographic image data with block matching method, as a calculating method of the amount of movement with reference to FIGS. 8A and 8B. With this calculating method, the amount of movement of the probe 2 is calculated as the amount of movement of the coordinates of the ROI 37 shown in FIG. 8B. First, the amount-of-movement calculating portion 35 has a correlation window 45 shown in FIG. 8A corresponding to two lines of the brightness values on the basis of the start point of the ROI 37 in the tomographic image data stored in the Pre frame memory 32. Incidentally, the size of the correlation window 45 can be arbitrarily determined. The brightness values of the lines are subjected to differentiating processing in the depth direction, and the ratio of change in brightness value is calculated. Further, the sum (DI, D2) of the calculated differentiated values is calculated for two lines. Further, the amount-of-movement calculating portion 35 performs the search operation plural times within an arbitrary search range of the tomographic image data that is stored in the Post frame memory 33 and is always updated. In addition, the amount-of-movement calculating portion 35 calculates the sum (DI', D2') of the differentiated values every one-time search, and further calculates ratios of K1=DI'/DI and K2=D2'/D2 with respect to the calculated DI and D2. A portion having the above-obtained results 1<1 and 1<2 that are the most approximate to 1 is considered as the moving destination, and the amount of movement (address after the movement) is estimated. In this case, results of 1<1>1 and 1<2>1 are not considered.

The amount of movement calculated by the amount-of-movement calculating portion 35 as mentioned above is output to the display unit 10 via the frame memory control portion 34. The display unit 10 moves the color elasticity image on the basis of the input amount of movement from among the monochrome tomographic image and the color elasticity image.

Figure 8B:
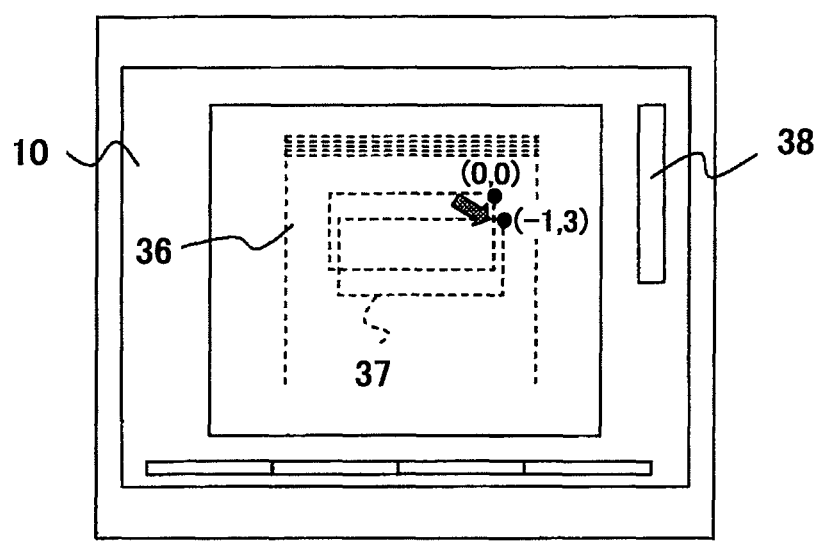
FIG. 8B is a diagram for illustrating moving operation of an ROI in the coordinate calculating section according to the second embodiment.

For example, as shown in FIG. 8B, upon moving the start point (0,0) of the ROI 37 to (−1,3), the start point (0,0) of the ROI 37, indicating the display start position or calculation start position of the ROI 37, is used for calculation as a parameter common to control software and hardware for actually executing signal processing. Further, upon displaying the position on the display unit 10, the ROT 37 is displayed on the basis of the start point (0,0). That is, as shown in FIG. 8A, upon calculating the movement of the start point (0,0) of the ROI 37 to (−1,3), the start point of the ROI 37 is moved to (−1,3) and the resultant point is displayed, as shown in FIG. 83.

In the above description, one correlation window 45 is set. Further, the number of the correlation window 45 is increased, thereby improving the precision for following operation. For example, when the number of the correlation window 45 is two, the ratio of the sum of the differentiated values of the correlation windows 45 is calculated, and the amount of movement is calculated by setting, as the moving destination, the portion having the ratio of the sum of the differentiated values of the correlation windows that is the most approximate to 1, thereby improving the precision for following operation.

For example, the magnetic sensor 11 attached to the probe 2 directly measures the amount of movement of the probe 2, the above-obtained amount of movement is input to the amount-of-movement calculating portion 35 of the coordinate calculating section 18, and the amount-of-movement calculating portion 35 may calculate the amount of movement of the ROI 37. Further, the amount-of-movement calculating portion 35 can output information, indicating the amount of movement is over the setting threshold, to the display unit 10 via the switching and adding unit 9, and can display the output data on the image shown in FIG. 8B. Moreover, referring to FIG. 8B, reference numeral 37 denotes an image display region, and reference numeral 38 denotes a color bar.

With the ultrasound diagnostic apparatus 1 according to the second embodiment, in addition to the advantages according to the first embodiment, the probe 2 is moved after inputting the freezing instruction. Thus, even if the tomographic image is moved, it is possible to correct and display the position of the color elasticity image with the following operation of the tomographic image. Therefore, upon stopping the increase/decrease in pressure to the body tissue and performing the paracentesis, the position of paracentesis can be specified without fail.

Third Embodiment

Herein, a description will be given of the support of the operation of the paracentesis needle for sampling the organ of the prostate cancer according to the third embodiment. According to the first and second embodiment, the operator specifies the lesion 115 as the paracentesis target on the basis of the elasticity image, and the advancing direction and position of the paracentesis needle 105 are adjusted on the basis of the specifying result. According to the third embodiment, in order to support the advancing operation of the paracentesis needle 105, upon advancing the paracentesis needle 105 along the jig, guide display operation indicating where the paracentesis needle 105 is in the lesion 115 is formed, and is displayed on the tomographic image or the elasticity image. That is, according to the third embodiment, referring to FIG. 9, an invasion device position calculating section 19 is arranged in parallel with the coordinate calculating section 18 shown in FIG. 1 and a transrectal-type hybrid probe is used as the probe 2. Others are the same as those according to the first embodiment and a description thereof is omitted.

Figure 10:
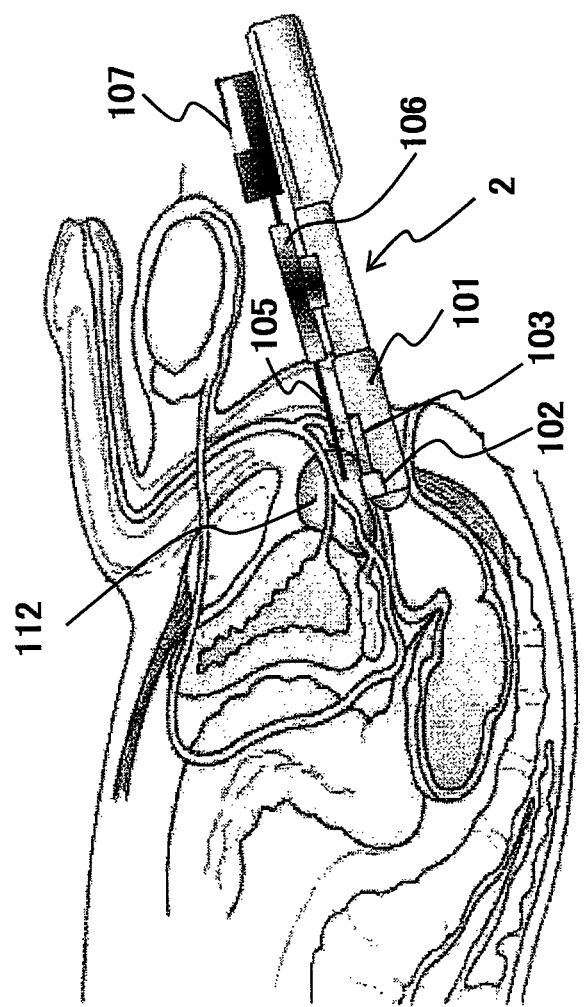
FIG. 10 is a diagram showing a state for using a hybrid probe for paracentesis of the prostate cancer.

FIG. 10 shows a state of the ultrasound diagnosis using a prostate 112 according to the third embodiment. As shown in FIG. 10, the probe 2 is a transrectal-type probe inserted into the body cavity, and is a hybrid probe comprising: a cylindrical base portion 101 that can be inserted into the body cavity of the subject; a probe 102 for transverse section that is formed by aligning a plurality of ultrasound vibrators in the circumferential direction of the base portion 101; and a probe 103 for longitudinal section obtained by aligning a plurality of ultrasound vibrators to the base portion 101 in the axial direction. According to the third embodiment, the probe 102 for transverse section has the plurality of ultrasound vibrators that are aligned along the direction of the ultrasound scanning surface (tomographic surface). The probe 103 for longitudinal section is formed by aligning a plurality of ultrasound vibrators in the orthogonal direction of the tomographic surface of the probe 102 for transverse section.

Referring to FIG. 10, the jig 106 having the paracentesis needle 105 is attached to the hybrid probe 2 according to the third embodiment. The jig 106 supports the paracentesis needle 105 to be capable of being advanced and returned in the orthogonal direction of the ultrasound output surface of the probe 102 for transverse section. Further, the dispenser 107 arranged to the rear end of the paracentesis needle 105 is operated so that the paracentesis needle 105 is invaded into the subject.

Transmitting signals from the transmuting unit 3 are alternately applied to the probe 102 for transverse section and the probe 103 for longitudinal section of the hybrid probe 2 according to the third embodiment. Further, the reflection echo signals received by the probe 102 for transverse section and the probe 103 for longitudinal section are alternately input to the receiving unit 4 and the phase shaping and adding unit 6, and the RF-signal frame data is individually fond and is output to the tomographic image constructing unit 7 to the elasticity image constructing unit 8.

The tomographic image constructing unit 7 restructures a lateral tomographic image on the basis of RF-signal frame data received by the probe 102 for transverse section, further restructures longitudinal and lateral tomographic images on the basis of the RF-signal frame data received by the probe 103 for longitudinal section, and displays the restructured images on the display unit 10 via the switching and adding unit 9. One example of the display image is shown in FIG. 11.

Figure 12:
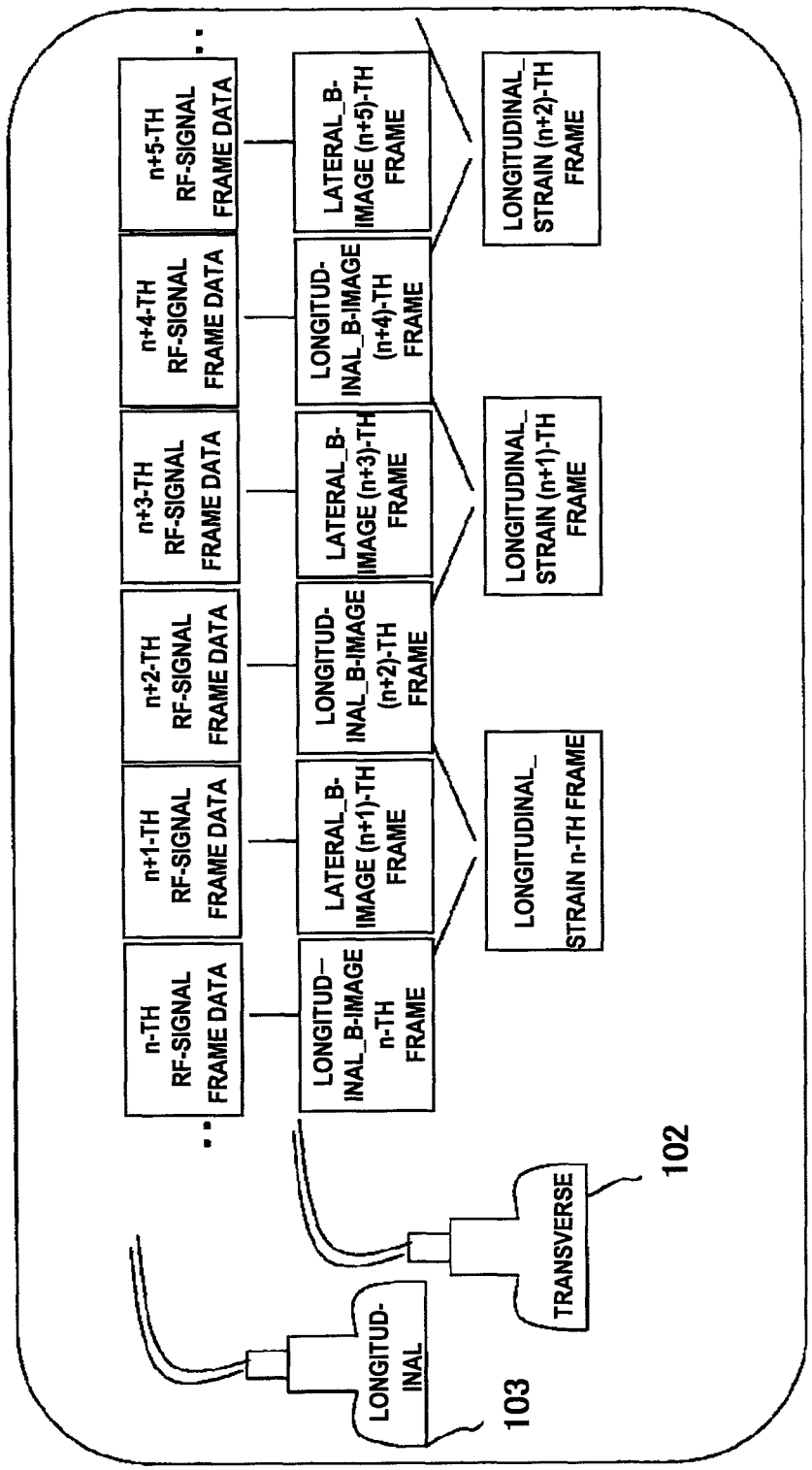
FIG. 12 is a diagram for illustrating a calculating example of displacement in an amount-of-displacement calculating section with a hybrid probe according to the third embodiment.

In the elasticity image constructing unit 8, upon selecting the longitudinal and lateral surface sides and calculating the displacement, referring to FIG. 12, the amount-of-displacement calculating section 14 selects RF-signal frame data that is obtained by thinning-out one piece of frame data, that is, the n-th RF-signal frame data and the (n+2)-th RF-signal frame data, longitudinal_strain frame data for calculating the displacement between a longitudinal 3-image n-th frame and a longitudinal_B-image (n+1)-th frame is formed. Upon selecting the transverse section and calculating the displacement, as shown in FIG. 12, the amount-of-displacement calculating section 14 selects the (n+1)-th RF-signal frame data and (n+3)-th RF-signal frame data, and forms lateral_strain frame data for calculating the displacement between lateral_B-image n-th frame and a lateral B-image (n+1)-th frame.

The strain/elastic-modulus calculating section 15 can calculate the strain or elastic modulus on the basis of the longitudinal or lateral strain frame data obtained by the amount-of-displacement calculating section 14, similarly to the first embodiment. According to the third embodiment, the strain corresponding to the lateral tomographic image is obtained on the basis of the lateral strain frame data. The color elasticity image corresponding to the lateral tomographic image is output to the switching and adding unit 9 via the strain/elastic-modulus analyzing section 16 and the color scanning converter section 17 on the basis of the strain data corresponding to the above-obtained lateral tomographic image.

Figure 11:
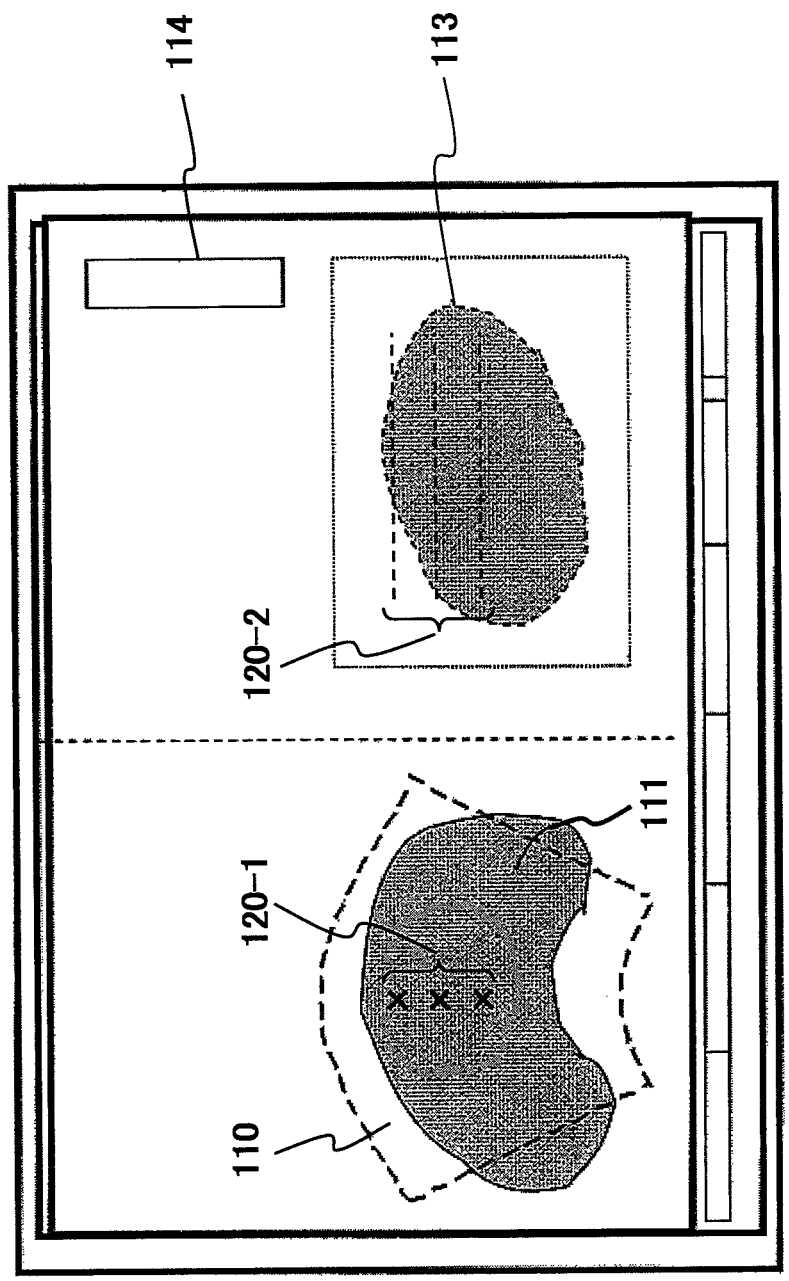
FIG. 11 is a diagram showing one example of a display image according to the third embodiment.

Referring to FIG. 11, the display unit 10 displays the lateral tomographic image 111 of the prostate at the left half of the screen and the longitudinal tomographic image 113 of the prostate at the right half of the screen. The color elasticity image 110 is superposed to the lateral tomographic image 111 and the resultant image is displayed on a fan-shaped region (ROI) of interest, shown by a dotted line. Reference numeral 114 denotes a color bar indicating a relationship between the level of elasticity and the image hue.

On the other hand, the invasion device position calculating section 19 obtains the advancing direction and position of the paracentesis needle 105 on the basis of the relatively positional relationship between the probe 2 and the paracentesis needle 105. Further, the position through which the end of the paracentesis needle 105 on the tomographic image upon advancing the paracentesis needle 105 is estimated on the basis of the tomographic image data captured from the monochrome signal processing section 12. Then, the estimated position through which the end of the paracentesis needle 105 is fond as guide display for displaying on the tomographic image or the elasticity image, and is output to the switching and adding unit 9.

Figure 13:
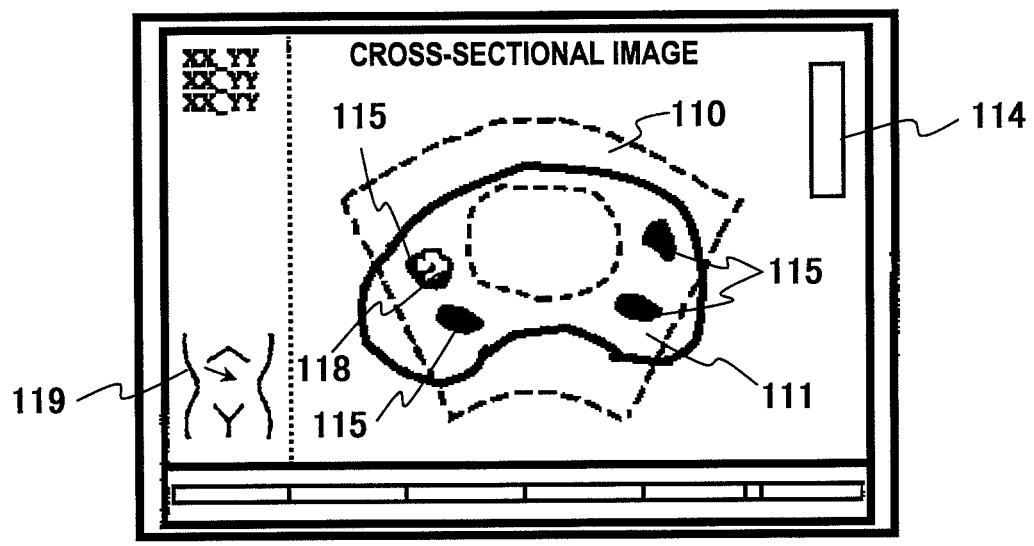
FIG. 13 is a diagram showing another example of the display image according to the third embodiment.

That is, the advancing and returning position of the paracentesis needle 105 has a fixed relative positional relationship to the probe 2, and the coordinates of the probe 2 and the tomographic image are relatively fixed. Then, the invasion device position calculating section 19 can calculate at which coordinate position of the displayed tomographic image passes through upon advancing the paracentesis needle 105 into the subject. Further, since a guide display 118 such as an outline x mark with as shown in FIG. 13, indicating the passing position of the paracentesis needle 105 is displayed on the lateral tomographic image, is formed, and is output to the switching and adding unit 9. The guide display 118 is superposed to the image and is displayed on the display unit 10.

Similarly, the passing position of the paracentesis needle 105 is displayed on the lateral tomographic image and the longitudinal tomographic image. Therefore, guide displays 120-1 and 120-2 shown by dotted lines in FIG. 11, indicating the passing position of the paracentesis needle 105 is formed and is superposed and displayed on the image. Referring to FIG. 11, the three guide displays 120-1 and 120-2 are displayed and, however, one of them is actually displayed corresponding to an angle 0.

Further, the probe 103 for longitudinal section captures the image of the paracentesis needle 105, and the paracentesis needle 105 is displayed on the longitudinal tomographic image. As a consequence, the operator operates the paracentesis needle 105 while directly observing the invasion position of the paracentesis needle 105 with the image, and samples the organ cell of a desired lesion.

Figure 14:
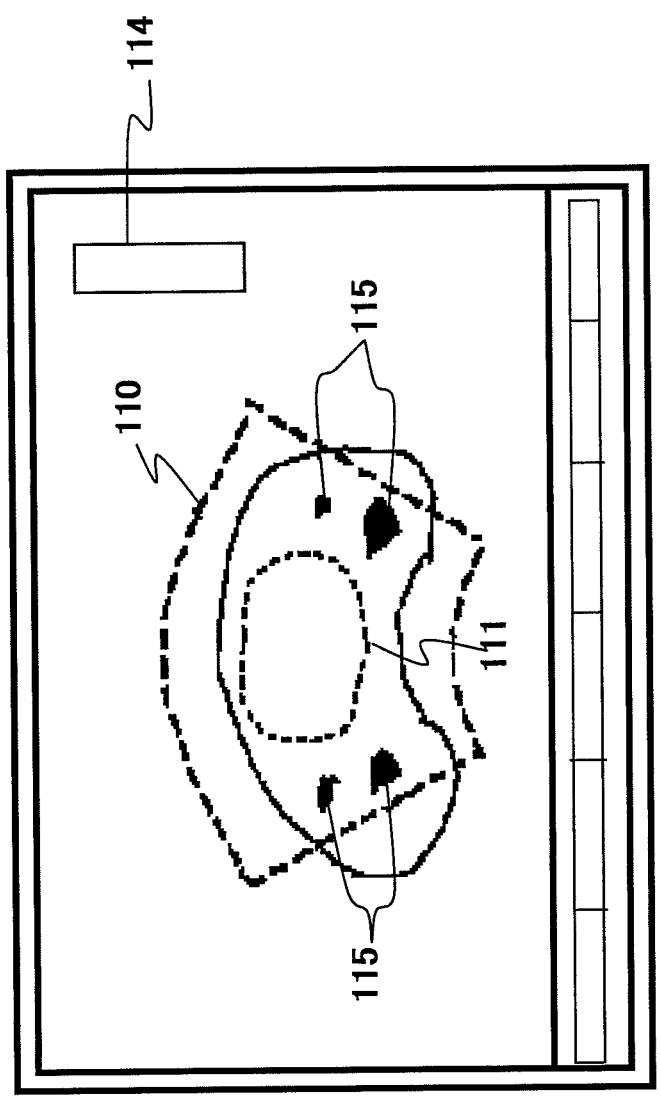
FIG. 14 is a diagram showing another example of the display image according to the third embodiment.

Hereinbelow, a description will be given of the supporting sequence of the operation of the paracentesis needle for sampling the organ of the prostate cancer with the above structure according to the third embodiment. Referring to FIG. 10, while the paracentesis needle 105 is pulled-out from the jig 106, the probe 2 is inserted in the rectum and pressure is applied to the prostate with the probe 2. Then, while increasing and decreasing the pressure to the prostate, ultrasonic waves are iteratively sent from the probe 2 at the time intervals, the lateral tomographic image and the longitudinal tomographic image are structured on the basis of the RF signal corresponding to the sent ultrasonic waves, and the resultant image is displayed on the display unit 10. Further, the color elasticity image corresponding to the lateral tomographic image, and the resultant image is superposed to the lateral tomographic image displayed on the display unit 10 and is displayed. FIGS. 11 and 14 show examples of the image displayed on the display unit 10 in this case. As shown in the drawings, the color elasticity image 110 is superposed to the lateral tomographic image 111 and the resultant image is displayed. Then, the lesion 115 having the hardened organ is displayed with, e.g., blue (B) and, therefore, the lesion 115 having the suspicion of the cancer is easily identified on the image. Further, the guide display 120-1 of the paracentesis needle 105 is superposed to the lateral tomographic image 111 and the resultant data is displayed and the guide display 120-2 is superposed to the longitudinal tomographic image 113 and the resultant data is displayed. Thus, the position of the probe 2 is adjusted so that the guide displays 120-1 and 120-2 match the position of the lesion 115. As a consequence, the paracentesis needle 105 can undergo the paracentesis into the lesion 115 without fail, thereby preparing the sampling of cell.

Next, in order to start the paracentesis operation of the paracentesis needle 105, a freezing instruction is input from the operation console 43, and the pressurizing operation of the subject with the probe 2 stops. Thus, the frozen color elasticity image 110 is displayed on the display unit 10. Then, the paracentesis needle 105 is invaded into the subject with the lesion 115 checked by the color elasticity image 110, the cell of the lesion 115 is sampled, and the paracentesis needle 105 is pulled-out.

That is, when the paracentesis needle 105 undergoes the paracentesis operation, the latest frozen elasticity image 110 is superposed to the monochrome tomographic image displayed in real time without pressurizing the subject. In particular, the guide display 120-1 of the paracentesis needle 105 is superposed to the lateral tomographic image ill and is displayed. Further, the guide display 120-2 is superposed to the longitudinal tomographic image 113 and is displayed. Therefore, the paracentesis operation can be performed while checking on the image that the guide displays 120-1 and 120-2 are positioned at the lesion 115 as the paracentesis target. As a consequence, the operation for performing the paracentesis of the paracentesis needle 105 to the specific lesion 115 can be supported, thereby improving the possibility of paracentesis.

Figure 15:
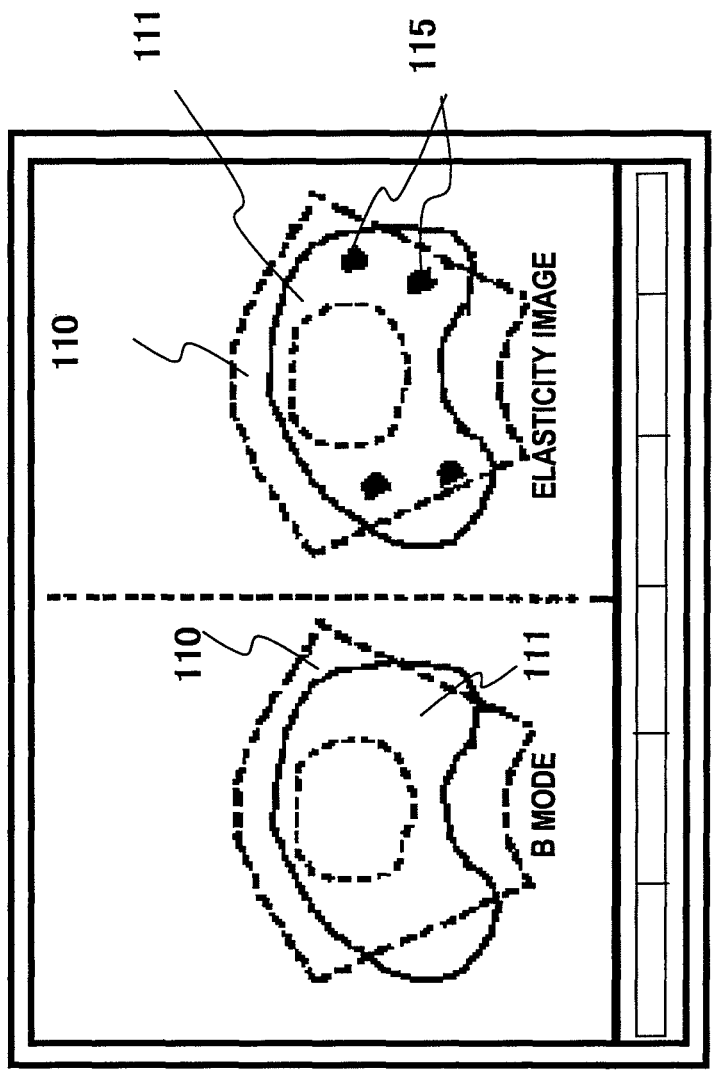
FIG. 15 is a diagram showing another example of the display image according to the third embodiment.
Figure 16:
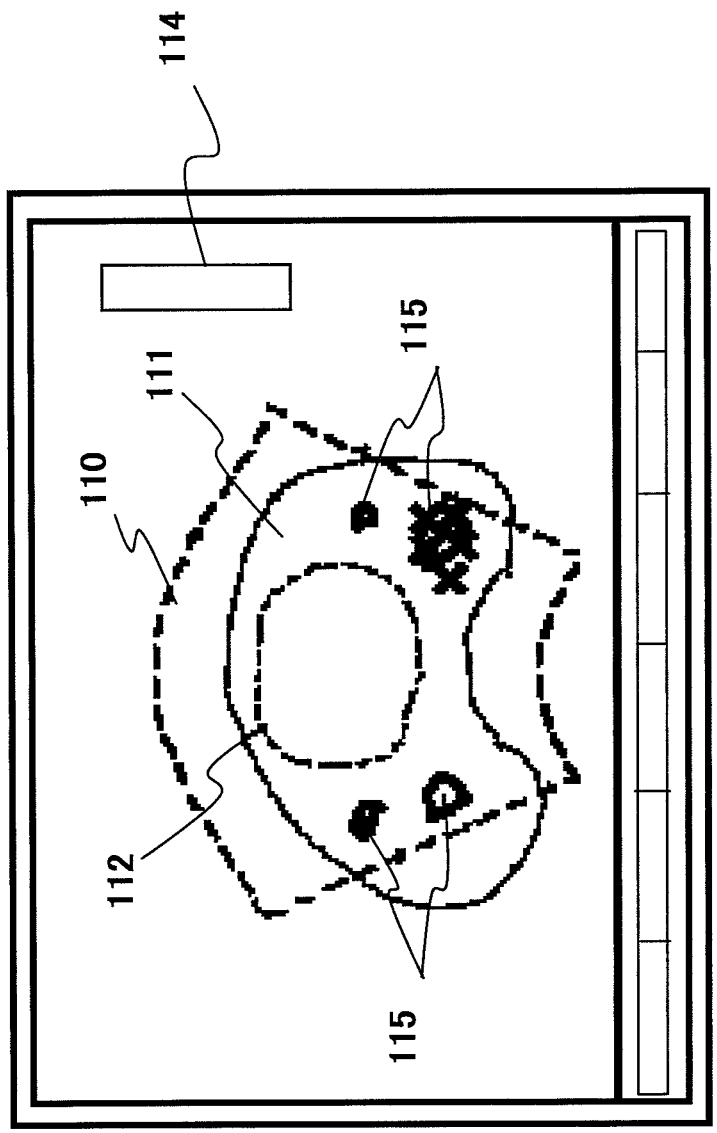
FIG. 16 is a diagram showing another example of the display image according to the third embodiment.
Figure 17:
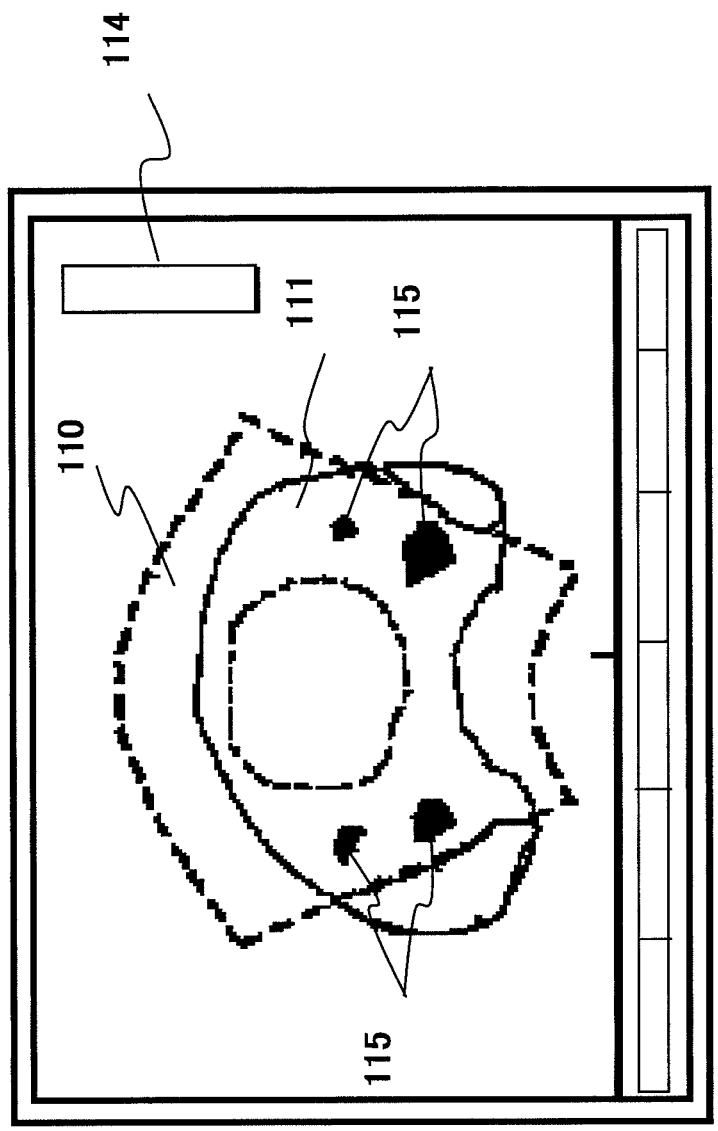
FIG. 17 is a diagram showing another example of the display image according to the third embodiment.

FIGS. 15 to 17 show other examples of the display image obtained according to the third embodiment. FIG. 15 shows an example in which the lateral tomographic image 111 is displayed at the left half of the screen obtained by the probe 102 for transverse section and the color elasticity image 110 subjected to the threshold processing corresponding to the lateral tomographic image 111 is superposed to the lateral tomographic image 111 and is displayed on the right half of the screen. Similarly, the longitudinal tomographic image obtained by the probe 103 for longitudinal section is displayed on the left side and the color elasticity image subjected to the threshold processing corresponding to the longitudinal tomographic image is superposed to the longitudinal tomographic image and is displayed on the right side.

Herein, in place of the display format of the lesion 115 shown in FIG. 15, referring to FIG. 16, the contour of the lesion 115 can be displayed. Alternatively, a mark such as a mark x can be displayed on the lesion 115. FIG. 17 shows an example in which, in place of displaying the lesion 115 shown in FIG. 15 with the color elasticity image subjected to the threshold processing, the color elasticity image 110 that relatively displays the level of elasticity without the threshold processing with colors is displayed.

According to the third embodiment, the freezing instruction and the freezing reset instruction are input from the operation console 43 by the operator. Instead of this, the jig 106 for supporting the paracentesis needle 105 has an advance/return detecting sensor that detects the advancing and returning position of the paracentesis needle 105. The advance/return detecting sensor can use an advance signal for detecting the advance start of the paracentesis needle 105. Similarly, a return signal indicating the end of return of the paracentesis needle 105, output from the advance/return detecting sensor can be used as a freezing reset instruction.

Fourth Embodiment

According to the first to third embodiments, the description is given of the example in which the operator operates the operation console 43 and inputs the freezing instruction input from the operation console 43 and of the example in which the signal detected by the advance/return detecting sensor arranged to the jig 106 that supports the paracentesis needle 105 is input to the operation console 43. However, the present invention is not limited to this and the freezing instruction can be input to the operation console 43 on the basis of the motion of the probe 2, as will be next described.

That is, as shown in FIG. 1, the probe 2 comprises the magnetic sensor 11 that detects the position and attitude of the probe 2 in cooperation with the three-dimensional magnetic field generated around the subject. The coordinate position calculating section 18 comprises a probe movement detecting portion that detects the movement of the probe 2 on the basis of the detection signal from the magnetic sensor 11. Then, the probe movement detecting portion determines that the paracentesis operation can start when the detected amount of movement of the probe 2 is not more than a preset threshold, and inputs the freezing instruction of the elasticity image to the operation console 43.

That is, according to the fourth embodiment, the operator fixes the probe 2 so as to start the paracentesis operation and the elasticity image is then automatically frozen. Therefore, the operation of the paracentesis can be convenient.

Fifth Embodiment

According to the fourth embodiment, the start of paracentesis operation of the operator is determined on the basis of the amount of movement of the probe 2. However, when the operator starts the paracentesis operation, the pressurization to the subject with the probe 2 generally stops.

Then, the pressure applied to the subject with the probe 2 is detected and, when the detected pressure is not more than the preset threshold, it is determined that the paracentesis operation can start. Further, the freezing instruction of the elasticity image is input to the operation console 43. Specifically, the probe 2 has a pressure sensor 20 that detects the pressure applied to the subject. Further, the strain/elastic-modulus calculating section 15 has a pressure measuring portion that measures the pressure applied to the subject on the basis of a pressure signal input from the pressure sensor 20. Furthermore, the change in pressure measured by the pressure measuring portion over time is monitored and, when the change in measurement pressure over time is not more than the setting threshold, a signal indicating this state is set as the freezing instruction, and is input to the operation console 43.

According to the fifth embodiment, the operator stops the pressurizing operation with the probe 2 so as to start the paracentesis operation and the elasticity image is then automatically frozen. As a consequence, the operation of paracentesis can be convenient.

Sixth Embodiment

Upon using the signal indicating that the amount of movement of the probe 2 or the pressure applied to the subject is not more than the threshold as the freezing instruction of the elasticity image according to the fourth and fifth embodiments, referring to FIG. 6 or 13, the display unit 10 displays a body mark 119 indicating the portion of the subject where the elasticity image is obtained and a probe mark 120 indicating the arrangement position of the probe 2 on the body mark 119. Further, the freezing control portion of the color scanning converter section 17 controls a threshold of pressure applied to a mover of the probe 2 or the subject in accordance with the arrangement position of the probe mark and the type of the body mark.

That is, since the elasticity characteristics of the organ of the subject are varied depending on the capturing portion, preferably, the threshold may be changed depending on the region of interest. In the case of an entirely soft portion, high pressure is required to transmit the pressure to the depth organ. Therefore, the threshold is preferably increased. On the other hand, in the case of a hard organ, since even excessively low pressure can be transmitted to the depth organ, the threshold is preferably reduced.

Similarly, the elasticity characteristics of the organ are varied depending on the age and sex of the subject. Then, preferably, the upper portion of patient information is input from the operation console 43 and the threshold is changed in accordance with the input patient information. In the case of women, since the organ is soft; the threshold is preferably increased. On the other hand, in the case of men, since the organ is hard, the threshold is preferably reduced. Incidentally, a single threshold can be controlled or a plurality of thresholds can be combined.

Seventh Embodiment

The first embodiment uses the example in which the elasticity image is frozen and displayed upon inputting the freezing instruction. However, the present invention is not limited to this. That is, the frame memory 29 of the color scanning converter 17 in the elasticity image constructing unit 8 stores a plurality of the elasticity images from among the elasticity images on time series. Then, the color scanning converter 17 can output at least one arbitrary elasticity image from among the plurality of elasticity images stored in the frame memory 29 to the switching and adding unit 9, and can display the output elasticity image on the display unit 10.

The operation console 43 has input means that displays a plurality of the elasticity images at different time on the display unit 10 and selects a desired elasticity image from among at least one of the displayed elasticity images. Then, the freezing control portion of the color scanning converter 17 can output the selected desired elasticity image, as the frozen elasticity image, to the switching and adding unit 9.

Eighth Embodiment

The above-mentioned embodiments show the examples in which the elasticity image is frozen. However, according to the present invention, the tomographic image of the superimposition image is frozen, thereby displaying the elasticity image on time series. That is, a tomographic image freezing instruction for freezing the display operation of the tomographic images on time series can be input to the operation console 43. In this case, the monochrome scanning converter 13 has a freezing control portion similar to the freezing control portion of the color scanning converter 17. The freezing control portion of the tomographic image selects the frozen tomographic image from the tomographic images on time series on the basis of the freezing instruction of the input tomographic image, and outputs the selected image to the switching and adding unit 9. Thus, the switching and adding unit 9 forms the superimposition images on time series of the frozen tomographic image and the elasticity images on time series, and displays the resultant images on the display unit 10.

According to the eighth embodiment, in the case of diagnosing the body tissue having the motion of the blood vessel as the region of interest, the elasticity image of the region of interest can be obtained. In this case, the observation of the change in elasticity image of the region of interest such as the blood vessel is required. On the other hand, the tomographic image is superposed and displayed as a reference image.

However, in the case of comparing the elasticity image with the tomographic image and observing both the images, both the images are changed in accordance with the motion of the organ. Therefore, the tomographic image can be an obstacle to the observation of the elasticity image.

On the other hand, according to the eighth embodiment, upon diagnosing the body tissue having the motion of the blood vessel as the region of interest, the freezing instruction of the tomographic image is input from the operation console 43. The position of the region of interest and the organ structure are displayed with the frozen tomographic image, and the elasticity of the region of interest can be observed with the elasticity image changing on time series. Therefore, this can contribute to the proper diagnosis. For example, upon obtaining the elasticity image of the organ, such as the blood vessel, which repeats the periodical contraction like the pulsation of the blood, the frozen tomographic image has a function of the reference image indicating the structure and position of the blood vessel. Further, with the technology disclosed in Japanese Unexamined Patent Application Publication No. 2004-141505, the tomographic image is frozen, thereby improving the frame rate of the elasticity image.

Ninth Embodiment

With the ultrasound diagnostic apparatus according to the present invention, the following ultrasound image display method can be employed. That is, the ultrasound image display method comprises: a step (a) of applying pressure to a subject; a step (b) of iteratively transmitting ultrasonic waves to the subject at time intervals and receiving reflection echo signals on time series corresponding to the iterative transmission of the ultrasonic waves; a step (c) of forming a tomographic image of the subject on the basis of the reflection echo signal; a step (d) of obtaining the displacement of the subject, caused by the pressure, on the basis of the reflection echo signal, and forming an elasticity image indicating the elasticity of parts in the body tissue on the basis of the obtained displacement; a step (e) of forming a superimposition image of the tomographic image and the elasticity image; a step (f) of displaying the superimposition image; a step (g) of displaying the superimposition images on time series by iterating the steps (a) to (f); a step (h) of inputting a freezing instruction for freezing the display operation on time series of any of the tomographic image and the elasticity image; a step (i) of selecting the frozen image on the basis of the freezing instruction; and a step (j) of forming the superimposition images on time series of the frozen image and the image displayed on time series.

In this case, in the step (h), the freezing instruction of the elasticity image for freezing the display operation on time series of the elasticity image is input. In the step (i), one of the formed plurality of elasticity images is selected as the frozen elasticity image on the basis of the freezing instruction of the elasticity image. In the step (j), the superimposition images obtained by the frozen elasticity image and the tomographic images displayed on time series are formed on time series and the resultant images are displayed.

Further, in the step (h), the freezing instruction of the tomographic image for freezing the display operation of the tomographic images on time series is input. In the step (i), one of the formed plurality of tomographic images is selected as the frozen elasticity image on the basis of the freezing instruction of the tomographic image. In the step (j), the superimposition images obtained by the frozen tomographic image and the elasticity images displayed on time series are formed on time series and the resultant images are displayed.

The invention claimed is:

1. An ultrasound diagnostic apparatus comprising:
an ultrasound probe for iteratively transmitting ultrasonic waves to a subject at time intervals, and receiving reflection echo signals from the subject corresponding to the transmitted ultrasonic waves;
a receiving-signal processing unit for processing the reflection echo signals received by the ultrasound probe;
a tomographic image constructing unit for forming tomographic images on a basis of the reflection echo signals;
an elasticity image constructing unit for obtaining displacement of body tissue of the subject, on a basis of the reflection echo signals, further obtaining an elasticity of parts in the body tissue on a basis of the obtained displacement, and forming elasticity images;
a freezing control portion adapted to select one of the elasticity images to be frozen on a basis of a freezing instruction, dependent upon a threshold, and to output the selected image as a selected frozen elasticity image, wherein the freezing control portion changes a threshold of pressure based on elasticity characteristics of an organ;
a superimposition-image forming unit adapted to form a series of superimposition images by superimposing the selected frozen elasticity image on a series of the tomographic images; and
a display unit for displaying the superimposition images, wherein
an elasticity image freezing instruction for freezing the display operation on a time series of the elasticity images is input to an input unit,
the freezing control portion selects the frozen elasticity image from the elasticity image on time series on a basis of the elasticity image freezing instruction, and outputs the selected image to the superimposition-image forming unit,
the superimposition-image forming unit forms the superimposition image from the time series of the frozen elasticity image and the tomographic image on time series,
an ultrasound probe movement detecting portion that detects a movement of the ultrasound probe on a basis of a position and attitude of the ultrasound probe in a three-dimensional coordinate system around the subject, and
a signal indicating that the movement of the ultrasound probe, output from the ultrasound probe movement detecting portion, is not more than a setting threshold, and is input to the input unit, as the elasticity image freezing instruction.

2. An ultrasound diagnostic apparatus comprising:
an ultrasound probe for iteratively transmitting ultrasonic waves to a subject at time intervals, and receiving reflection echo signals from the subject corresponding to the transmitted ultrasonic waves;
a receiving-signal processing unit for processing the reflection echo signals received by the ultrasound probe;
a tomographic image constructing unit for forming tomographic images on the basis of the reflection echo signals;
an elasticity image constructing unit for obtaining a displacement of body tissue of the subject, on the basis of the reflection echo signals, further obtaining an elasticity of parts in the body tissue on a basis of the obtained displacement, and forming elasticity images;
a freezing control portion adapted to select one of the elasticity images to be frozen on a basis of a freezing instruction, dependent upon a threshold, and to output the selected image as a selected frozen elasticity image, wherein the freezing control portion changes a threshold of pressure based on elasticity characteristic of an organ;
a superimposition-image forming unit adapted to form a series of superimposition images by superimposing the selected frozen elasticity image on a series of the tomographic images; and
a display unit for displaying the superimposition images, wherein an elasticity image freezing instruction for freezing the display operation on time series of the elasticity images is input to an input unit,
the freezing control portion selects the frozen elasticity image from the elasticity image on time series on a basis of the elasticity image freezing instruction, and outputs the selected image to the superimposition-image forming unit, and
the superimposition-image forming unit forms the superimposition image on time series of the frozen elasticity image and the tomographic image on time series,
the ultrasound diagnostic apparatus comprises a pressure measuring portion that measures pressure applied to the subject, and
a signal indicating the time change of the pressure, output from the pressure measuring portion, is not more than a setting threshold, and is input to the input unit, as the elasticity image freezing instruction.

3. The ultrasound diagnostic apparatus according to claim 1, wherein a tomographic image freezing instruction for freezing the display operation on time series of the tomographic image is input to the input unit,
the freezing control portion selects the frozen tomographic image from the tomographic images on time series on a basis of the tomographic image freezing instruction, and outputs the selected image to the superimposition-image forming unit, and
the superimposition-image forming unit forms the superimposition image on time series of the frozen tomographic image and the elasticity image on time series.

4. The ultrasound diagnostic apparatus according to claim 2, wherein the input unit comprises input means that inputs the elasticity image freezing instruction.

5. An ultrasound diagnostic apparatus comprising:
an ultrasound probe for iteratively transmitting ultrasonic waves to a subject at time intervals, and receiving reflection echo signals from the subject corresponding to the transmitted ultrasonic waves;
a receiving-signal processing unit for processing the reflection echo signals received by the ultrasound probe;
a tomographic image constructing unit for forming tomographic images on the basis of the reflection echo signals;
an elasticity image constructing unit for obtaining s displacement of body tissue of the subject, on the basis of the reflection echo signals, further obtaining an elasticity of parts in the body tissue on a basis of the obtained displacement, and forming elasticity images;
a freezing control portion adapted to select one of the elasticity images to be frozen on a basis of a freezing instruction, dependent upon a threshold, and to output the selected image as a selected frozen elasticity image, wherein the freezing control portion changes a threshold of pressure based on an elasticity characteristic of an organ;

a superimposition-image forming unit adapted to form a series of superimposition images by superimposing the selected frozen elasticity image on a series of the tomographic images; and a display unit for displaying the superimposition images, wherein an elasticity image freezing instruction for freezing the display operation on a time series of the elasticity images is input to an input unit, the freezing control portion selects the frozen elasticity image from the elasticity image on time series on a basis of the elasticity image freezing instruction, and outputs the selected image to the superimposition-image forming unit, the superimposition-image forming unit forms the superimposition image on a time series of the frozen elasticity image and the tomographic image on time series, wherein the ultrasound probe comprises a jig to which an invasion device is attached, the jig detects the advance/return of the invasion device to the subject on a basis of a position and attitude of the invasion device in a three-dimensional coordinate system around the subject, and an advance signal of the invasion device indicating that the movement of the and invasion device, output from the jig, and is input to the input unit, as the elasticity image freezing instruction.

6. The ultrasound diagnostic apparatus according to claim 2, wherein the display unit displays a body mark indicating a portion of the subject, for obtaining the elasticity image, and a probe mark indicating an arrangement position of the ultrasound probe on the body mark, and the freezing control portion controls the setting threshold in accordance with a type of the body mark and the arrangement position of the probe mark.

7. The ultrasound diagnostic apparatus according to claim 2, wherein the freezing control portion controls the setting threshold in accordance with information on the subject.

8. The ultrasound diagnostic apparatus according to claim 2, wherein the freezing control portion selects, as the frozen elasticity image, the elasticity image at the time for inputting the freezing instruction from the elasticity images on time series, and outputs the selected image to the superimposition-image forming unit.

9. The ultrasound diagnostic apparatus according to claim 2, wherein the elasticity image forming unit comprises a frame memory that stores a plurality of the elasticity images from the elasticity image on time series, the display unit displays at least one of the plurality of elasticity images stored in the frame memory, the input unit comprises means that selects a desired one from at least one of the displayed elasticity images, and the freezing control portion outputs the selected desired elasticity image as the frozen elasticity image to the superimposition-image forming unit.

10. The ultrasound diagnostic apparatus according to claim 1, wherein the input unit inputs a freezing reset instruction for resetting the freezing operation displayed on time series, and the freezing control portion outputs the images on time series whose display operation on time series is frozen to the superimposition-image forming unit on a basis of the freezing reset instruction.

11. The ultrasound diagnostic apparatus according to claim 1, further comprising:

an amount-of-movement calculating section that calculates an amount of movement of the tomographic image after inputting the freezing instruction from the tomographic image from the time for inputting the freezing instruction, wherein the superimposition-image forming unit moves a position of the frozen elasticity image to match a position of the tomographic image after the freezing instruction by using the amount of movement.

12. The ultrasound diagnostic apparatus according to claim 1, further comprising:

an amount-of-movement calculating section that calculates an amount of movement of the tomographic image after inputting the freezing instruction from the tomographic image from the time for inputting the freezing instruction, wherein the superimposition-image forming unit outputs a warning message indicating the amount of movement is over a setting threshold.

13. The ultrasound diagnostic apparatus according to claim 2, wherein the ultrasound probe is a hybrid ultrasound probe comprising a cylindrical basic portion that can be inserted in the body cavity of the subject, and an ultrasound probe for transverse section having arrangement of a plurality of ultrasound vibrators in a direction parallel with a tomographic surface and an ultrasound probe for longitudinal section having arrangement of a plurality of ultrasound vibrators in a direction orthogonal to the tomographic surface at an end of the basic portion, a jig to which an invasion device is attached supports the invasion device to be capable of advance and return in a direction orthogonal to an ultrasound emission surface of the ultrasound probe for transverse section, the tomographic image constructing unit forms a lateral tomographic image on a basis of the reflection echo signal corresponding to the ultrasound probe for transverse section, and further forms a longitudinal tomographic image on the basis of the reflection echo signal corresponding to the ultrasound probe for longitudinal section, and the elasticity image constructing unit forms the elasticity image on the basis of the reflection echo signal corresponding to the ultrasound probe for transverse section.

14. An ultrasound image display method comprising:
(a) iteratively transmitting ultrasonic waves to a subject at time intervals, and receiving reflection echo signals from the subject corresponding to the transmitted ultrasonic waves;
(b) processing the received reflection echo signals;
(c) forming tomographic images on a basis of the reflection echo signals;
(d) obtaining a displacement of body tissue of the subject, on a basis of the reflection echo signals, obtaining an elasticity of parts in the body tissue on a basis of the obtained displacement, and forming elasticity images;
(e) selecting one of the elasticity images to be frozen on a basis of a freezing instruction, which depends upon a threshold and outputting the selected elasticity image as a frozen image, by controlling a threshold of pressure based on a hardness of an organ,
(f) forming a series of superimposition images by superimposing the frozen elasticity image on a series of the tomographic images; and
(g) displaying the superimposition images.

15. The ultrasound image display method according to claim 14, wherein, in steps (f) and (g), the superimposition images of the frozen elasticity image and the series of tomographic images displayed in real time.

16. An ultrasound diagnostic apparatus comprising:

- an ultrasound probe for iteratively transmitting ultrasonic waves to a subject at time intervals, and receiving reflection echo signals from the subject corresponding to the transmitted ultrasonic waves;
- a receiving-signal processing unit for processing the reflection echo signals received by the ultrasound probe;
- a tomographic image constructing unit for forming tomographic images on a basis of the reflection echo signals;
- an elasticity image constructing unit for obtaining displacement of body tissue of the subject, on a basis of the reflection echo signals, further obtaining an elasticity of parts in the body tissue on a basis of the obtained displacement, and forming elasticity images;
- a freezing control portion adapted to select one of the elasticity images to be frozen on a basis of a freezing instruction, and to output the selected image as a selected frozen elasticity image;
- a superimposition-image forming unit adapted to form a series of superimposition images by superimposing the selected frozen elasticity image on a series of the tomographic images; and
- a display unit for displaying the superimposition images;
- wherein the display unit displays a body mark indicating a portion of the subject, for obtaining the elasticity image, and a probe mark indicating an arrangement position of the ultrasound probe on the body mark, and
- the freezing control portion controls a setting threshold which is used as guidance in limiting application of the ultrasonic probe, in accordance with a type of the body mark and the arrangement position of the probe mark.

* * * * *